(12) United States Patent
Hillson et al.

(10) Patent No.: US 8,697,388 B2
(45) Date of Patent: Apr. 15, 2014

(54) HEAVY METAL BIOSENSOR

(75) Inventors: Nathan J. Hillson, San Francisco, CA (US); Lucille Shapiro, Stanford, CA (US); Ping Hu, San Ramon, CA (US); Gary L. Andersen, Berkeley, CA (US)

(73) Assignee: U.S. Department of Energy, Washington, DC (US)

( * ) Notice: Subject to any disclaimer, the term of this patent is extended or adjusted under 35 U.S.C. 154(b) by 608 days.

(21) Appl. No.: 12/526,312

(22) PCT Filed: Feb. 6, 2008

(86) PCT No.: PCT/US2008/001620
§ 371 (c)(1),
(2), (4) Date: Jan. 25, 2011

(87) PCT Pub. No.: WO2008/127496
PCT Pub. Date: Oct. 23, 2008

(65) Prior Publication Data
US 2011/0117590 A1    May 19, 2011

Related U.S. Application Data

(60) Provisional application No. 60/900,628, filed on Feb. 8, 2007.

(51) Int. Cl.
*C12Q 1/02*    (2006.01)
*G01N 33/20*    (2006.01)

(52) U.S. Cl.
USPC ............ 435/29; 436/73; 436/81; 536/23.1

(58) Field of Classification Search
None
See application file for complete search history.

(56) References Cited

PUBLICATIONS

Liao et al. Environmental Pollution, vol. 142, issue 1, Jul. 2006, p. 17-23.*
Passarge, Eberhard. Color Atlas of Genetics, p. 202-203, Thieme Medical Publishers, 1995.*

* cited by examiner

*Primary Examiner* — Oluwatosin Ogunbiyi
(74) *Attorney, Agent, or Firm* — John D. Cravero; Brian J. Lally; John T. Lucas

(57) ABSTRACT

Compositions and methods are provided for detection of certain heavy metals using bacterial whole cell biosensors.

18 Claims, 4 Drawing Sheets

HEAVY METAL BIOSENSOR

CROSS-REFERENCE TO RELATED APPLICATIONS

This application claims priority to, is a national stage application of, PCT Application No. PCT/US2008/001620 filed on Feb. 6, 2008, which claims priority of U.S. Provisional Patent Application No. 60/900,628, filed on Feb. 8, 2007, both of which are hereby incorporated in their entireties.

STATEMENT OF GOVERNMENTAL SUPPORT

This invention was made during work supported by the U.S. Department of Energy under Contract No. DE-AC02-05CH11231. Therefore, the United States Government has certain rights in this invention.

REFERENCE TO SEQUENCE LISTING

The electronic readable copy and paper copy of the sequence listings for this invention are identical.

BACKGROUND OF THE INVENTION

Potentially hazardous levels of heavy metals have dispersed into subsurface sediment and groundwater in a number of metal-contaminated sites and represent a challenge for environmental restoration. This contamination can cause severe risks to human health due to direct metal uptake into vegetables and due to spreading via wind or via infiltration in the groundwater or via flooding. The concentrations and distribution of metals are influenced by the intrinsic binding capacity of the soil via ion-exchange (on clay), adsorption to functional groups (on organic matter), precipitation (due to pH changes) and co-precipitation (on iron oxy-hydroxides), as well as integration in the mineral lattice. In addition, microorganisms play a role in the fate of metals resulting in such bio-geochemical processes as biosorption on biomass, bio-precipitation due to oxidation or reduction reactions, precipitation with sulfides, obtained through sulfate reduction etc.

Effective bioremediation of these sites requires knowledge of genetic pathways for resistance and biotransformation by component organisms within a microbial community. However, a comprehensive understanding of bacterial mechanisms of heavy metal toxicity and resistance has yet to be achieved. While many metals are essential to microbial function, heavy metals, i.e., most of those with a density above 5 g/cm$_3$, have toxic effects on cellular metabolism.

The majority of heavy metals are transition elements with incompletely filled d orbitals providing heavy metal cations which can form complex compounds with redox activity. Therefore, it is important to the health of the organism that the intracellular concentrations of heavy metal ions are tightly controlled. However, due to their structural and valence similarities to nontoxic metals, heavy metals are often transported into the cytoplasm through constitutively expressed nonspecific transport systems. Once inside the cell, toxic effects of heavy metals include nonspecific intracellular complexation, with thiol groups being particularly vulnerable. Interactions of these nonspecific complexes with molecular oxygen leads to the formation of reactive oxygen species such as $H_2O_2$, resulting in oxidative stress within the cell. In addition to oxidative stress, complexation of sulfhydryl groups with heavy metal cations results in reduced activity of sensitive enzymes.

In order to achieve effective remediation, there is an acute need to develop new methods of assessing the heavy metal concentrations in natural and industrial environments. Existing methods for heavy metal detection including spectroscopical methods, such as AAS, AES, ICP-MS, etc.; or electrochemical methods, such as ISE, polarography, etc. These methods, however, can be expensive or not useful when there is a need to detect metals at low concentrations. Moreover, these methods can only detect the total amount of heavy metals and not the bioavailable concentrations accessible to the living organisms. Therefore, development of new and inexpensive methods for detection of bioavailable heavy metal concentrations is highly desirable.

Biosensors are useful analytical devices in this respect, and various have been described for heavy metal detection. Biorecognition elements may include whole cells, e.g. bacteria, fungi, lichens, mosses, etc.; or proteins, e.g. enzymes, apoenzymes, antibodies, etc. Transducers may be potentiometric, amperometric, optic, conductometric, spectrophotometric, etc. Currently available bioluminescent methods to assess ecotoxicity include naturally luminescent marine bacteria, primarily the MICROTOX system (AZUR Environmental).

An ideal assessment method for the presence of heavy metals is inexpensive, easy to use, and sensitive. Improved compositions and methods for assessment of toxic metals, including uranium, are of great interest. The present invention addresses these issues.

Relevant Literature

Liao et al. (2006) Environ Pollut. 142(1):17-23. Assessment of heavy metal bioavailability in contaminated sediments and soils using green fluorescent protein-based bacterial biosensors. Shetty et al. (2003) Anal Bioanal Chem. 376 (1):11-7. Luminescence-based whole-cell-sensing systems for cadmium and lead using genetically engineered bacteria. Shetty et al. (2004) Biotechnol Bioeng. 5; 88(5):664-70. Fluorescence-based sensing system for copper using genetically engineered living yeast cells.

Hu et al. (2005) J Bacteriol. 187(24):8437-49. Whole-genome transcriptional analysis of heavy metal stresses in *Caulobacter crescentus*. Southward and Surette (2002) Mol Microbiol. 45(5):1191-6. The dynamic microbe: green fluorescent protein brings bacteria to light.

U.S. Pat. No. 6,210,948, Expression and secretion of heterologous polypeptides from *caulobacter*.

SUMMARY OF THE INVENTION

Compositions and methods are provided for the biological detection of heavy metals, including uranium. A genetically engineered microorganism is provided as a biosensor. The biosensor organism becomes fluorescent in the presence of one or more of cadmium, chromate, dichromate, plutonium, and uranium. Certain promoters provided herein are highly specific for presence of the uranyl cation, a soluble form of uranium. The genetically engineered microorganism comprises at least one heavy metal responsive element, which comprises a polynucleotide sequence encoding a fluorescent reporter protein operably linked to a promoter sequence that is active in presence of these heavy metals, and inactive in its absence.

In some embodiments the microorganism comprises a single heavy metal responsive element. The element may be selectively responsive to a specific metal. In other embodiments the microorganism comprises a plurality of heavy metal responsive elements, e.g. two, three or more. In such embodiments the fluorescent reporter proteins are desirably distinguishable from each other in the wavelength of emitted light.

In some embodiments of the invention, the promoter sequence is a promoter sequence of a heavy metal responsive protein of a *Caulobacter* species. Such promoters include, without limitation, the promoter sequences of *Caulobacter* proteins CC3302; CC1777; CC3500; CC1532; and CC3291, or a homolog or variant thereof. The genetically engineered microorganism may be a *Caulobacter* species, for example *Caulobacter crescentus*, or any other microorganism in which heavy metal responsive *Caulobacter* promoters are appropriately activated.

In some embodiments of the invention, the fluorescent reporter protein is a green fluorescent protein (GFP). A GFP variant of interest includes a GFP that is excited by UV light, and that emits light in the visible spectrum. In one such embodiment, the fluorescent reporter protein is GFPuv, which is excited by 366 nm ultraviolet light, and emits green light at 509 nm. The UV excitation light is nearly invisible to the naked eye, while the green emitted light is easily visible. This allows the user of the invention to shine a UV lamp on a GFPuv producing bacterial culture, and thereby to directly observe the emission of green light, without the need for special optical filters. Where a plurality of single heavy metal responsive elements are provided in the microorganism, various light emitting proteins may be used, e.g. CFP, YFP, mCherry, and the like.

The biosensor organism is useful in detecting the presence of heavy metals in water or soil samples. In one embodiment, the biosensor organism is contacted with soil and/or groundwater in situ, allowed to change color, and used to localize the extent of the contamination at the site of interest. Following assessment of heavy metals, the site may be subjected to bioremediation or other methods of reducing the presence of heavy metals.

BRIEF DESCRIPTION OF THE DRAWINGS

These and other objects, features and many of the attendant advantages of the invention will be better understood upon a reading of the detailed description of the invention when considered in connection with the accompanying drawings which show as follows.

DETAILED DESCRIPTION OF THE EMBODIMENTS

Figure 1:
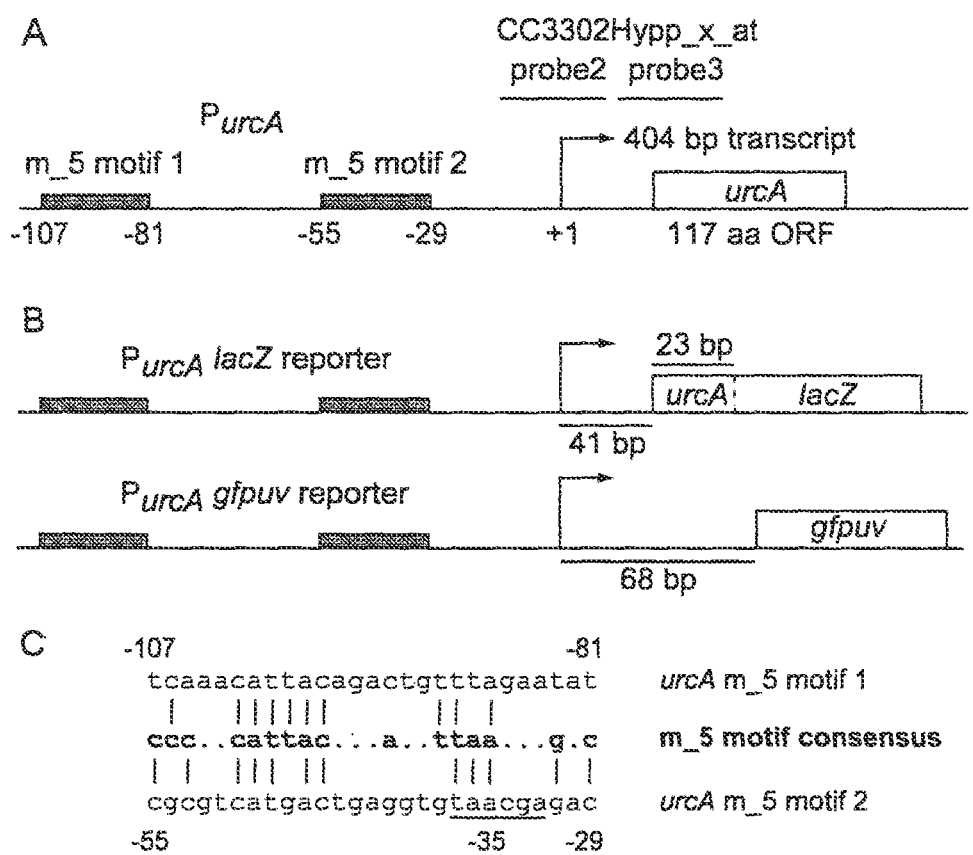
FIG. 1. urcA promoter region and $P_{urcA}$ reporter schematics. (A) CC3302Hypp_x_at probe 3 is the most upstream probe in the Affymetrix array to match the 404 base pair urcA transcript (13), placing the +1 transcriptional start site approximately 5 to 15 (10 as shown) base pairs from the end of the immediately adjacent probe 2. The locations of the tandem uranium inducible m__5 motifs within the urcA promoter are shown as grey boxes, with indicated base pair numbering relative to the putative +1 site. (B) The $P_{urcA}$ lacZ and $P_{urcA}$ gfpuv reporters utilize the urcA promoter, replacing urcA with an urcA/lacZ translational fusion, or gfpuv, respectively. (C) The two sequence matches within the urcA promoter to the m__5 motif consensus are presented, with vertical lines indicating identity. The underlined −35 region of the promoter overlaps the second urcA m__5 motif.

Compositions and methods are provided for the biological detection of heavy metals with a biosensor organism comprising at least one heavy metal responsive element, which comprises a polynucleotide sequence encoding a fluorescent reporter protein operably linked to a promoter sequence that is active in presence of these heavy metals, and inactive in its absence. Vectors of interest include plasmids, viruses capable of expression in bacterial cells, and the like. The biosensor organism becomes fluorescent in the presence of one or more of cadmium, chromate, dichromate, plutonium and uranium. The promoter of the heavy metal responsive element may be a promoter sequence of a heavy metal responsive protein of a *Caulobacter* species, e.g. *Caulobacter crescentus* CC3302, CC1777; CC3500; CC1532; and CC3291, or a homolog or variant thereof.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed herein are standard methodologies well known to one of ordinary skill in the art.

Other objects, features and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991).

The term "gene" is well understood in the art and includes polynucleotides encoding a polypeptide. In addition to the polypeptide coding regions, a gene may includes non-coding regions including, but not limited to, introns, transcribed but untranslated segments, and regulatory elements upstream and downstream of the coding segments.

The terms "polypeptide", "peptide" and "protein" are used interchangeably to refer to polymers of amino acids of any length. These terms also include proteins that are post-translationally modified through reactions that include glycosylation, acetylation and phosphorylation.

An "effective amount" is an amount sufficient to effect beneficial or desired results. An effective amount can be administered in one or more administrations.

A promoter is understood to be the sequences generally located upstream of a coding sequence, which sequences are sufficient to initiate transcription of an operably linked coding sequence. Promoters may include motifs, as known in the art, for polymerase binding, and may further include sequences that provide for activation of the promoter in the presence of a heavy metal of interest. In bacterial cells, the region controlling overall regulation can be referred to as the operator. Promoters for use in bacterial systems also usually contain a Shine-Dalgarno (S.D.) sequence operably linked to the coding sequence. Promoters typically fall into two classes, inducible and constitutive. Inducible promoters are promoters that initiate increased levels of transcription from DNA under their control in response to some change in culture conditions, e.g., the presence or absence of a metal. A promoter that is native to the biosensor organism may be used, or a heterologous promoter may be used.

The presence of a saturating concentration of the heavy metal will increase expression of the reporter gene at least about 2-fold, preferably at least about 5-fold, preferably at least about 10-fold, more preferably at least about 20-fold, more preferably at least about 50-fold, more preferably at least about 100-fold, more preferably at least about 200-fold, even more preferably at least about 400- to about 500-fold, even more preferably at least about 1000-fold, when compared to the expression of the same promoter and reporter gene in the substantial absence of the metal. Methods for measuring levels (whether relative or absolute) of expression are known in the art.

The activity of a responsive element generally depends upon the presence of transcriptional regulatory factors and/or the absence of transcriptional regulatory inhibitors. Transcriptional activation can be measured in a number of ways known in the, but is generally measured by detection and/or quantitation of mRNA or the protein product of the coding sequence under control of (i.e., operatively linked to) the responsive element. A responsive element can be of varying lengths, and of varying sequence composition.

The heavy metal responsive elements of the present invention generally include a promoter that is upregulated in the presence of one or more heavy metals of interest. The promoter may be selective for uranium, cadmium, plutonium, or chromium ions, or may be non-selective with respect to these ions. Promoters of particular interest include the promoter elements regulating the following *Caulobacter crescentus* sequences:

| Annotation | Fold-Change in Expression | | | | Gene |
| --- | --- | --- | --- | --- | --- |
| | Cadmium | Chromate | Dichromate | Uranium | |
| CC1777 | 18.9 | 14.1 | 8.6 | 2.9 | Superoxide dismutase (cofactor, Mn2) (sodA) |
| CC3500 | 2.9 | 8.5 | 6.7 | 2.3 | TonB-dependent outer membrane receptor |
| CC1532 | 3.2 | 3.8 | 3.6 | 2 | Conserved hypothetical protein |
| CC3291 | 6.6 | 3.9 | 2.8 | 2.2 | Hypothetical protein |
| CC3302 | 1 | 1 | 1 | 27.5 | urcA |

Metal concentrations used for stress: cadmium: 6 µM; potassium chromate: 40 µM; potassium dichromate: 27 µM (contains 54 µM chromium); uranium: 200 µM.

In some embodiments of the invention, the promoter component of the heavy metal responsive element contains at least about 50 nucleotides, at least about 100 nucleotides, at least about 200 nucleotides, at least about 500 nucleotides or more of the non-coding sequence upstream of any one of CC3302, CC1777, CC3500, CC1532 or CC3291, or a homolog or variant thereof. The length of sequence will be sufficient to provide for a change in expression in an operably linked coding sequence in the presence of one or more heavy metals.

In some embodiments of the invention, the promoter is *Caulobacter crescentus* CC3302 promoter, the sequence of which may be found in Genbank at accession number AE005992.1 SEQ ID NO: 27, *Caulobacter crescentus* CB15 section 318 of 359 of the complete genome subsection 7998-8971. Usually the promoter will include at least one uranium-specific promoter motif sequence. CC3302/urcA has two repeats of this motif, occurring approximately 150 bp and 100 bp upstream of the protein ATG start codon for CC3302/urcA (about nucleotides 8822-8849 SEQ ID NO: 28, and 8874-8901 SEQ ID NO: 29). For example, a promoter of interest may include at least about 200 bp upstream of the start ATG codon, or nucleotides 8771-8971 SEQ ID NO: 30 of the *C. crescentus* genome sequence recited above.

Promoters of interest provide for a biosensor organism with a detection limit (sensitivity) of at least about 5 µM concentration of the metal of interest, and may provide for a detection limit of about 2.5 µM; of about 1 µM; of about 0.5 µM; or may detect concentrations of less than about 0.5 µM, or less than about 0.25 µM. The detection limit is influenced by the choice of reporter protein, for example a GFP reporter may be about 2-fold more sensitive than a non-fluorescent reporter, such as lacZ.

A variant of a heavy metal responsive promoter is a heavy metal responsive promoter that differs from the provided sequences, but still retains metal regulated activity. The difference in sequence can be due to differences in linear sequence, arising from, for example, single base mutation(s), addition(s), deletion(s), and/or modification(s) of the bases.

The degree of sequence identity between the provided, or wild-type sequence and a variant or homolog sequence may be at least about 80%, at least about 85%, at least about 90%, at least about 95%, or more. Sequence identity can be determined by a sequence comparison using, i.e., sequence alignment programs that are known in the art, such as those described in Current Protocols in Molecular Biology (F. M. Ausubel et al., eds., 1987) Supplement 30, section 7.7.18, Table 7.7.1 A preferred alignment program is ALIGN Plus (Scientific and Educational Software, Pennsylvania), preferably using default parameters. Alternatively, hybridization under stringent conditions can also indicate degree of sequence identity. Stringent conditions are known in the art; an example of a stringent condition is 80° C. (or higher temperature) and 6×SSC (or less concentrated SSC). Other hybridization conditions and parameters (in order of increasing stringency) are: incubation temperatures of 25° C., 37° C., 50° C., and 68° C.; buffer concentrations of 10×SSC, 6×SSC, 1×SSC, 0.1×SSC (where 1×SSC is 0.15 M NaCl and 15 mM citrate buffer) and their equivalents using other buffer systems; formamide concentrations of 0%, 25%, 50%, and 75%; incubation times from about 24 hours about 5 minutes; 1, 2, or more washing steps; wash incubation times of 1, 2, or 15 minutes; and wash solutions of 6×SSC, 1×SSC, 0.1×SSC, or deionized water.

Nucleic acids of the invention also include naturally occurring variants of the nucleotide sequences (e.g., degenerate variants, allelic variants, etc.). Variants of the nucleic acids of the invention are identified by hybridization of putative variants with nucleotide sequences disclosed herein, preferably by hybridization under stringent conditions. For example, by using appropriate wash conditions, variants of the nucleic acids of the invention can be identified where the allelic variant exhibits at most about 25-30% base pair (bp) mismatches relative to the selected nucleic acid probe. In general, allelic variants contain 15-25% by mismatches, and can contain as little as even 5-15%, or 2-5%, or 1-2% by mismatches, as well as a single by mismatch.

The invention also encompasses homologs corresponding to the sequences that encode the sequences, where the source of homologous genes can be any species, particularly bacterial species, e.g. *Caulobacter* species.

The nucleic acids of the invention can be provided as a linear molecule or within a circular molecule, and can be provided within autonomously replicating molecules (vectors) or within molecules without replication sequences. The nucleic acids of the invention can be introduced into suitable host cells using a variety of techniques available in the art, such as transferrin polycation-mediated DNA transfer, transfection with naked or encapsulated nucleic acids, liposome-mediated DNA transfer, intracellular transportation of DNA-coated latex beads, protoplast fusion, viral infection, electroporation, gene gun, calcium phosphate-mediated transfection, and the like.

The metal response promoter element is operably linked to a reporter sequence. The reporter can be any gene expressed in the host cell that provides a directly or indirectly detectable characteristic; that is, that confers a detectable phenotype upon the host cell. Exemplary phenotypes include change in color, fluorescence, antibiotic resistance and/or sensitivity, luminescence, etc., e.g. a polynucleotide sequence encoding a fluorescent protein, a protein that provides for a colorimetric change, and the like. In some embodiment, reporters can luminesce or fluoresce, in vivo, without the addition of an exogenous substrate. A particularly suitable reporter is green fluorescent protein. Green fluorescent protein ("GFP") is a polypeptide derived from an apopeptide having 238 amino acid residues and a molecular weight of approximately 27,000. GFP contains a chromophore formed from amino acid residues 65 through 67. As its name indicates, GFP fluoresces; it does not bioluminesce like luciferase. In vivo, the chromophore of GFP is activated by energy transfer from coelenterazine complexed with the photoprotein aquorin, with GFP exhibiting green fluorescence at 510 nm. Upon irradiation with blue or UV light, GFP exhibits green fluorescence at approximately 510 nm. A preferred variant of GFP is excited by ultraviolet light, at about 366 nm wavelength, and emits green light in the visible range, at about 509 nm.

Modified variants of green fluorescent protein, e.g., EGFP, EBFP, EYFP, d2EGFP, ECFP, GFPuv are included within the term green fluorescent protein. These variants of GFP are commercially and known in the art. Furthermore, GFP and variants thereof, are provided in the following references, all of which are incorporated by reference: Chalfie, M. et al. (1994) Science 263:802-805; Prasher, D. C., et al. (1992) Gene 111:229-233; Inouye, S. & Tsuji, F. I. (1994) FEBS Letters 341:277-280; Wang, S. & Hazelrigg, T. (1994) Nature 369:400-403; Cody, C. W., et al. (1993) Biochemistry 32:1212-1218; Inouye, S. & Tsuji, F. I. (1994) FEBS Letters 351:211-214; Heim, R., et al. (1994) Proc. Natl. Acad. Sci., USA 91:12501-12504; Yang, T. T., et al. (1996) Nucleic Acids Res. 24(22): 4592-4593; Cormack, B. P., et al. (1996) Gene 173:33-38; Crameri, A., et al. (1996) Nature Biotechnol. 12:315-319; Haas, J. et al, (1996) Curr. Biol. 6:315-324; Galbraith, D. W., et al. (1995) Methods Cell Biol. 50:1-12; Living Colors Destabilized EGFP Vectors (April 1998) CLONTECHniques XIII(2):16-17, Living Colors pEBFP Vector (April 1997) CLONTECHniques XII(2):16-17; Heim, R. & Tsien, R. Y. (1996) Curr. Biol. 6:178-182; Ormö, et al. (1996) Science 273:1392-1395; Mitra, R. D. et al. (1996) Gene 173:13-17. EBFP is optimized for expression in mammalian cells whereas BFP2, which retains the original jellyfish codons, can be expressed in bacteria. The GFP-like chromophores from EBFP and BFP2 can usefully be included in the vectors of the present invention. Analogously, EYFP ("enhanced yellow fluorescent protein"), contains four amino acid substitutions, different from EBFP, Ormö et al., *Science* 273: 1392-1395 (1996), that shift the emission from green to yellowish-green. Citrine, an improved yellow fluorescent protein mutant, is described in Heikal et al., *Proc. Natl. Acad. Sci. USA* 97:11996-12001 (2000). ECFP ("enhanced cyan fluorescent protein") contains six amino acid substitutions, one of which shifts the emission spectrum from green to cyan. Heim et al., *Curr. Biol.* 6:178-182 (1996); Miyawaki et al., *Nature* 388:882-887 (1997). The GFP-like chromophore of each of these GFP variants can usefully be used. The GFP-like chromophore can also be drawn from other modified GFPs, including those described in U.S. Pat. Nos. 6,124,128; 6,096,865; 6,090,919; 6,066,476; 6,054,321; 6,027,881; 5,968,750; 5,874,304; 5,804,387; 5,777,079; 5,741,668; and 5,625,048, the disclosures of which are incorporated herein by reference in their entireties.

An alternative to fluorescent reporters is provided by enzymes that provide for a colorimetric change. For example, the LacZα gene product encodes an active β-galactosidase, readily detectable colorimetrically when the cells are induced with the cognate heavy metal, e.g. uranium. Bacteria containing the active form are blue in the presence of the metal and the chromogenic enzyme substrate 5-bromo-4 chloro-3-indolyl-β-D-galactoside (X-Gal); and red when grown on IPTG-supplemented MacConkey agar. A wide variety of assays for β-galactosidase activity—calorimetric, fluorescent, and luminescent—are known, and can readily be used. For example, o-nitrophenyl-.beta.-D-galactopyranoside (ONPG) and chlorophenol red β-d-galactopyranoside are conveniently used as substrates for spectrophotometric detection, typically in liquid medium. Fluorescein di-β-D-galactopyranoside ("FDG", "fluorescein digalactoside") is a sensitive substrate for detecting β-galactosidase fluorescently. A chemiluminescent substrate for β-galactosidase (Roche, GALACTON™ Plus β-gal substrate) is also available commercially.

A green fluorescent protein of particular interest is GFPuv, which is the "cycle 3" variant described by Crameri et al. (1996) Nature Biotech. 14(3):315-9, herein specifically incorporated by reference.

The activity of reporter proteins may be influenced by the presence of certain heavy metals. Where cadmium is present, a LacZ reporter may show an increase of activity at concentrations of greater than about 10 μM, although the reporter has little cross specificity with nitrate (<400 μM), lead (<150 μM) and chromium (<41.6 μM). Concentrations of cadmium greater than about 10 μM may also reduce activity of a GFP reporter, although the reporter is unaffected by significant concentrations of nitrate (<400 μM), lead (<150 μM), or cadmium (<41.6 μM). Where high concentrations of cadmium or chromium are suspected in a sample, the assessment for the presence of other metals may require calibration to correct for an inhibition of activity, depending on the choice of reporter. Alternatively, a combination of biosensor microorganisms may be used, where the reporter proteins have different sensitivities to metal concentrations.

In the present invention, a fluorescent reporter gene is operably linked to a heavy metal responsive promoter to provide one or more heavy metal responsive element(s), which elements are introduced in a microbial cell to create a biosensor organism. The DNA encoding the heavy metal responsive element(s), particularly the promoter sequences, may be obtained from any library prepared from suitable cells, prepared from various sources according to the desired effect. The sequences may also be obtained by oligonucleotide synthesis. Libraries may be screened with probes (such as oligonucleotides of about 20-80 bases) designed to identify the promoter of interest. Screening the cDNA or genomic library with the selected probe may be conducted using standard procedures as described in Sambrook et al, Molecular Cloning: A Laboratory Manual (New York: Cold Spring Harbor Laboratory Press, 1989). An alternative means to isolate the promoter is to use PCR methodology.

The one or more heavy metal responsive element sequences may be inserted into a replicable vector for expression. Many such vectors are available. The vector components generally include, but are not limited to, one or more of the following: an origin of replication, one or more marker genes, an enhancer element, a promoter, and a transcription termination sequence. Where the host cell is a *Caulobacter* cell, broad host range vectors capable of being expressed in *Caulobacter* are readily constructed and introduced to *Caulobacter* by electroporation. At a low but practicable frequency, homologous recombination of the incoming heavy metal responsive element with the chromosome-resident copy of the promoter in the cell will result in a gene rescue or transfer event. In some cases it may be desirable to obtain a stable cell line in which the heavy metal responsive element is chromosomal.

Vectors may contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media.

Construction of suitable vectors containing one or more of the above-listed components employs standard ligation techniques. Isolated plasmids or DNA fragments are cleaved, tailored, and re-ligated in the form desired to generate the plasmids required. For analysis to confirm correct sequences in plasmids constructed, the ligation mixtures are used to transform host cells, and successful transformants selected by ampicillin or tetracycline resistance where appropriate. Plasmids from the transformants are prepared, analyzed by restriction endonuclease digestion, and/or sequenced.

Numerous techniques are known and are useful according to the invention for delivering vectors or other polynucleotides described herein to cells, including the use of nucleic acid condensing agents, electroporation, complexing with asbestos, polybrene, DEAE cellulose, Dextran, liposomes, cationic liposomes, lipopolyamines, polyornithine, particle bombardment and direct microinjection (reviewed by Kucherlapati and Skoultchi, 1984; Keown et al., 1990; Weir, 1999; Nishikawa and Huang, 2001).

Suitable cells for expressing the DNA in the vectors herein are typically microbial cells. Suitable prokaryotes for this purpose include eubacteria, such as Gram-negative or Gram-positive organisms, for example, *Caulobacter*, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *S. enteritica*; *Serratia*, e.g., *Serratia marcescans*, and *Shigella*, as well as Bacilli such as *B. subtilis* and *B. licheniformis*, Pseudomonads such as *P. aeruginosa*, *P. putida*, and *Streptomyces*. These examples are illustrative rather than limiting.

*Caulobacter* spp. are extremely ubiquitous and are able to survive in low-nutrient environments. They have been found in freshwater, seawater, soil, ground water, wastewater, deep-sea sediment, and a deep subsurface gold mine and have been noted for their ability to survive in broad environmental habitats where contamination may be present. In addition, *Caulobacter crescentus* has been shown to form high-density biofilms with the potential for use in bioreactors for bioremediation and has been used as a model organism to study cell cycle control. The bacteria alternate between a stalked cell that is attached to a surface, and an adhesive motile dispersal cell that searches to find a new surface upon which to stick and convert to a stalked cell. The bacteria attach tenaciously to nearly all surfaces and do so without producing the extracellular enzymes or polysaccharide, "slimes" that are characteristic of most other surface attached bacteria.

*Caulobacter* species are of interest as a source of heavy metal responsive promoter elements, and are also of particular interest as a biosensor host organism. Species of interest include, without limitation, *Caulobacter fusiformis*, *Caulobacter henricii*, *Caulobacter segnis*, *Caulobacter spinosum*, *Caulobacter vibrioides* ("*Caulobacter crescentus* str. CB15"), *Caulobacter crescentus*, etc.

The biosensor bacterium can express a non-natural reporter protein that produces a visible signal. The visible signal can be light, which can be, for example, in the form of luminescence. The visible signal can also be the result of production of a pigment as a result of expression of nucleic acid encoding the reporter protein. The nucleic acid that encodes the reporter protein can encode more than one protein, the expression of which results in a detectable signal. These genes may be simultaneously or sequentially expressed, depending on the promoter which controls their expression within the construct. Thus, the term "reporter protein" can describe one protein that is sufficient to produce the signal, or more than one protein, which when expressed sequentially or simultaneously or with some temporal overlap, produces the signal.

Recipients of a construct that encodes a bioluminescent reporter protein with high light output can be chosen by visual examination of resulting colonies on agar plates. Using strains that produce easily visible light, it is possible to determine the assessment of samples without the use of light detecting equipment, although light detecting devices may be used for continuous, on-line monitoring of light output and for detecting quantitative changes in the degree of light emitted. Examples of such light detecting devices can include, but are not limited to, devices which transmit light, such as a liquid light pipe or fiber optic cable, coupled to a device which measures light, such as, for example, a photomultiplier or photodiode.

In some embodiments of the invention, whole-cell bacterial cadmium biosensor are used. Compositions of such bacterial cells include suspension of bacteria in a physiologicically acceptable excipient; frozen suspensions; and freeze-dried, or lyophilized suspensions. Such cells can maintain significant activity after lyophilization and reconstitution in a physiologically acceptable buffer. Such compositions provide for enhanced on-demand usability in the field.

The biosensor organism of the present invention, comprising one or more heavy metal responsive element(s), is used in a method of assessing the levels of heavy metals in a sample or at a site. Such methods may comprise contacting the sample or site with a biosensor bacterium of the present invention; detecting the expression of the reporter protein by the biosensor bacterium; and correlating a reduction in the expression of the reporter protein with the presence of the heavy metal(s) of interest. In some embodiments, the heavy metal is uranium. In other embodiments, two or more of uranium, cadmium, plutonium and chromium are detected, either with a single heavy metal responsive element; with an organism engineered to comprise a plurality of heavy metal responsive elements where each element is responsive to a different metal; or with a plurality of organisms where each organism is responsive to a different metal. Typically the methods will include the use of control samples, which may be a known positive control, e.g. having a defined concentration of the metal to be assessed; and/or a negative control known to have an absence of the metal. The light output of the biosensor bacterium can be determined according to the methods described herein for measuring light output of bioluminescent microorganisms.

Where the samples are analyzed off site, an apparatus may be used for assessment. The apparatus can comprise: a first chamber, containing a biosensor bacterium of the present invention; means in fluid communication with the first chamber for sample delivery; and means in photometric proximity to the first chamber for delivering light at a wavelength excitatory for the targeted fluorescent protein and means for detecting light output from the biosensor bacterium, whereby an increase in light output detects the presence of the metal.

In some embodiments of the invention, the biosensor bacterium are used in situ. In situ assessment of objects, e.g. contaminated shipping containers, manufacturing facility, etc.; environmental sites and compositions, e.g. soil, sediments, water, etc., is performed on the contaminated region. The biosensor bacteria of the invention are sprayed or otherwise brought into contact with the potentially contaminated objects, sites, compositions, etc. The bacteria are left for a period of time sufficient to activate the heavy metal responsive promoter and to express the reporter construct, usually at least about 1 hour, at least about 2 hours, at least about 4 hours, 12 hours, at least about one day or more. The biosensor bacteria are then exposed to ultraviolet light, and the resulting emission of green light detected visually or with a light detecting device. In some embodiments the site may be photographed or otherwise recorded, where the recording is optionally available for scanning and documentation.

Site assessment may alternatively sink observation wells in a grid pattern covering the region and taking water samples from the wells or collecting soil samples in a grid pattern covering the region. The sample containing one or more environmental contaminants can include soil, sediment, sludge, water, or combinations thereof. Analysis is conducted on these samples to determine the concentration of metals and type of metals at the various locations in the contaminated region.

Sites that are determined to be contaminated may be subject to bioremediation. For example, the site may be monitored for the presence of, and if necessary to provide, metal reducing organisms. This may be accomplished by sprinkling or spraying a liquid solution comprising the organisms on the surface of the contaminated region and allowing the liquid to permeate through the region. Alternatively, injection wells or other forms of conduits may be utilized. If the sample is in a subsurface environment, such as groundwater, the contacting step can include injecting a liquid into the subsurface environment using, for example, drive-point devices. Alternatively, recirculation wells can be used.

Suitable organisms for biomediation comprise the ability to reduce Cr(VI) to Cr(III); and/or U(VI) to U(IV). The organisms may be provided as an isolate; or as a consortium of organisms. If desired, nutrients, such as phosphorus- and nitrogen-containing compounds, can be provided to the sample containing the contaminants to support microbial activity. Such nutrients can be added to the sample as separate compounds or they can be engineered into the compound having at least one hydrolysable organic group.

Anaerobic bioremediation by anaerobic bacteria may also find use, for example in an above ground bioreactor. Contaminated soil can also be excavated and placed in a bioreactor. Above ground or ex situ bioremediation of aquifers frequently involves "pump and treat" operations which process and treat large volumes of contaminated ground water by use of one or more bioreactors. Generally, ex situ bioremediation of soil or water is performed by transferring the soil or water, or combinations thereof, to a bioreactor treatment process where a significant degree, if not all, of the biotransformation occurs. The organism is added to a bioreactor or upstream thereof. The amount of the organism which is added is preferably an amount that is effective to enhance biotransformation of the halogenated contaminant.

The bioremediation method can be monitored by measuring the initial concentration of a contaminant and monitoring its degradation into transformation products. This latter step can be accomplished by measuring the decrease in concentration of the contaminant of interest and/or the increase in concentration or partial pressure of its transformation products during the degradation of the environmental contaminant.

The transformation products typically include less hazardous, preferably innocuous, compounds and ions, for example less soluble forms of uranium.

The present invention provides methods and kits for assessing environmental contaminants in a sample of soil, sediment, sludge, water, or combinations thereof. For example, the sample containing an environmental contaminant can include subsurface water or soil, which can be treated either in situ or ex situ. A kit may include one or more biosensor bacterium, and instructions for use. The kit may further comprise a source of light, e.g. UV light; a light detection means; and positive and/or negative controls.

Although this invention has been described primarily in terms of the assessment of uranium, it is clearly envisaged that the organisms; genetic sequences and polypeptides of this invention may also be useful for detection of other metals.

EXPERIMENTAL

Material and Methods

Reagents. T4 DNA ligase, shrimp alkaline phosphatase (SAP) and endonucleases were purchased from Fermentas (Hanover, Md.) and New England Biolobs (Ipswich, Mass.). DNA oligos were purchased from the Stanford Protein and Nucleic Acid Biotechnology Facility (Stanford, Calif.). One Shot Top10 chemically competent *E. coli* and 0.1 cm electroporation cuvettes were purchased from Invitrogen (Carlsbad, Calif.). DNA sequencing was performed by Sequetech (Mountain View, Calif.). KOD Hot Start DNA polymerase was purchased from Novagen (Madison, Wis.). DNA miniprep and gel extraction kits were purchased from Qiagen (Valencia, Calif.). The ND-3300 Fluorospectrometer was purchased from NanoDrop (Wilmington, Del.). Depleted uranyl nitrate was purchased from Sigma-Aldrich, and a stock solution was prepared as described previously (Hu, P., E. L. Brodie, Y. Suzuki, H. H. McAdams, and G. L. Andersen. 2005. Whole-genome transcriptional analysis of heavy metal stresses in *Caulobacter crescentus*. J Bacteriol 187:8437-8449).

Cloning of the urcA Promoter LacZ Reporter.

The genomic region containing the urcA (cc3302) promoter was amplified from *Caulobacter* CB15N genomic DNA with KOD Hot Start DNA polymerase and oligos NJH144 and NJH121. The 50 µL PCR reaction mixture, containing 5% DMSO, was made per the manufacturer's protocol. The PCR reaction was initiated by 1 min 45 sec melting at 94° C., followed by 32 cycles of 15 sec melting at 94° C., 30 sec annealing at 58° C., and 1 min 10 sec extension at 68° C. This product was then purified by electrophoresis through 1.2% agarose, followed by gel extraction and then reamplified with oligos NJH120 and NJH121 as described above. This second PCR product was then then digested with BglII and KpnI (protocol as directed by manufacturer), ligated overnight at 16° C. with T4 DNA ligase (protocol as directed by manufacturer) with similarly digested pPR9TT vector (Santos, P. M., I. Di Bartolo, J. M. Blatny, E. Zennaro, and S. Valla. 2001. New broad-host-range promoter probe vectors based on the plasmid RK2 replicon. FEMS Microbiol Lett 195:91-96) backbone, and then transformed into One-Shot Top10 chemically competent *E. coli* cells (protocol as directed by manufacturer). The sequence of the resulting plasmid, pNJH123, was confirmed by primer extension sequencing using oligos NJH155 and NJH156.

urcA Promoter LacZ Reporter *Caulobacter* Strains.

*Caulobacter crescentus* CB15N Δcc1634 (strain LS4358) was transformed with plasmid pNJH123 by electroporation as previously described to yield the urcA promoter LacZ reporter strain NJH199. The in frame Δcc1634 deletion reduces the background β-galactosidase activity of *Caulobacter*.

urcA Promoter LacZ Reporter Activity Assays.

Cultures of strain NJH199 were grown at 28° C. in M2G media. Overnight cultures were diluted to an $OD_{660\,nm}$ of 0.1 with fresh M2G, and then grown for an additional 2 hr at 28° C. to resume exponential growth before stressing the cells with either mock treatment or 200 µM uranyl nitrate. The stressed cultures were then grown for 2 hr before liquid culture β-galactosidase assays were conducted, as previously described (Miller 1972. Experiments in Molecular Genetics, Cold Spring Harbor Lab, NY).

$P_{urcA}$ gfpuv Reporter Strain.

An NcoI/NheI DNA fragment containing gfpuv was amplified from plasmid pBAD-GFP. An NcoI restriction site internal to gfpuv was silently mutated using the splicing by overlap extension (SOE) method. pBAD-GFP template was amplified with KOD Hot Start DNA polymerase using oligos NJH122 and NJH237 (5' SOE PCR reaction) or NJH236 and NJH123 (3' SOE PCR reaction), as described above. These first round SOE PCR products were mixed 1:1 as template for the second round SOE PCR reaction, and then amplified using oligos NJH122 and NJH123, as described above. This second round SOE PCR product was then digested with NcoI and NheI.

An AscI/NcoI DNA fragment containing the urcA promoter was amplified from plasmid pNJH123 with KOD Hot Start DNA polymerase using oligos NJH144 and NJH238. This PCR product was then digested with AscI and NcoI, ligated with the NcoI/NheI digested gfpuv fragment (described above) and AscI/NheI digested low copy pRVYFP-2 vector (M. Thanbichler, unpublished) backbone (triple ligation), and then transformed into OneShot Top10 chemically competent *E. coli* cells. The sequence of the resulting plasmid, pNJH193, was confirmed by primer extension sequencing using oligos NJH237 and NJH244.

In an effort to enhance folding and stability, we added a $His_6$ tag to the N-terminus of GFPuv. To do this, oligos NJH246 and NJH247, 100 pmol/µL each, were mixed 1:1 in a 50 µL total volume, heated at 94° C. for 2 min and then annealed at room temperature. This annealed mixture of NJH246/247 was diluted 1:400, and then mixed 1:1 with NcoI-digested/SAP-treated pNJH193 vector backbone for ligation. This ligation mixture was then transformed into OneShot Top10 chemically competent *E. coli* cells. The sequence of resulting plasmid, pNJH198, was confirmed by primer extension sequencing using oligo NJH241.

In an attempt to increase the strength of the ribosomal-binding site (RBS) within pNJH198, we added the RBS through start ATG codon of pRKLac290 in frame with the $His_6$GFPuv protein sequence of pNJH198. To do this, oligos NJH248 and NJH249, 100 pmol/µL each, were mixed 1:1 in a 50 µL total volume, heated at 94° C. for 2 min and then annealed at room temperature. This annealed mixture of NJH248/249 was diluted 1:400, and then mixed 1:1 with NcoI-digested/SAP-treated pNJH198 vector backbone for ligation. This ligation mixture was then transformed into OneShot Top10 chemically competent *E. coli* cells. The sequence of resulting plasmid, pNJH200, was confirmed by primer extension sequencing using oligo NJH241.

To place the urcA promoter GFPuv reporter into a higher-copy number plasmid, we amplified an AscI/SpeI DNA fragment from plasmid pNJH200 with KOD Hot Start DNA polymerase using oligos NJH144 and NJH239, as described above except the extension time was 1 min 45 sec. This PCR product was then then digested with AscI and SpeI, and ligated with similarly digested pBVMCS-2 vector backbone, and then transformed into OneShot Top10 chemically competent E. coli cells. The sequence of the resulting plasmid, pNJH201, was confirmed by primer extension sequencing using oligos NJH240, NJH241, NJH242 and NJH243. Caulobacter crescentus CB15N (strain LS101) was transformed with plasmid pNJH201 by electroporation as previously described to yield the urcA promoter GFPuv reporter strain NJH371.

urcA Promoter GFPuv Reporter Caulobacter Strains.

Caulobacter crescentus CB15N (strain LS101) was transformed with plasmid pNJH201 by electroporation as previously described to yield the urcA promoter GFPuv reporter strain NJH371.

urcA Promoter GFPuv Reporter Activity Assays.

Cultures of strain NJH371 were grown overnight at 28° C. in M2G media (Ely 1991. Genetics of Caulobacter crescentus. Methods Enzymol 204:372-384) to an $OD_{660\,nm}$ of about 0.4 before stressing the cells with either mock treatment or 200 µM uranyl nitrate. The stressed cultures were then grown for 4 hr before measuring the GFPuv fluorescence intensity with a ND-3300 Fluorospectrometer, exciting with the UV LED, and monitoring emission at 509 nm, as directed by the manufacturer.

$P_{xyl}$ gfpuv Strain.

pBAD-GFPuv was digested with EcoRI, followed by a 1 hour limited digest with NdeI (gfpuv contains an internal NdeI site), to afford the desired 900 bp band containing full-length gfpuv which was isolated by gel electrophoresis. The NdeI/EcoRI gfpuv fragment was ligated with similarly digested pX31, a pBBR1MCS-based vector containing 500 bp of the xylose promoter inserted in front of the unique NdeI site, and then transformed into OneShot Top10 chemically competent E. coli cells. Caulobacter crescentus CB15N was transformed with the resulting plasmid, pNJH153, by electroporation as previously described to yield the $P_{xyl}$ gfpuv strain NJH250.

$P_{urcA}$ gfpuv Reporter Activity Assays.

Cultures of strain NJH371 ($P_{urcA}$ gfpuv) were grown overnight at 28° C. in M2G media to an $OD_{660\,nm}$ of about 0.4. These cultures were then stressed with the addition of either mock treatment, or indicated concentrations of uranyl nitrate, sodium nitrate, lead nitrate, cadmium sulfate and/or potassium chromate (FIGS. 3C, 3D and 3E); or, the 1:1 (by volume) addition of M2G media, or uranium contaminated (4.2 µM) or uncontaminated (<0.1 µM) variants of Oak Ridge Field Research Center ground water sample FW231-17 (FIG. 4), optionally supplemented with 50 µM uranyl nitrate. The stressed cultures were then grown on an orbital shaker for 4 hours (FIGS. 3D, 3E and 4) or the amount of time indicated (FIG. 3C) before measuring the GFPuv fluorescence intensity with a ND-3300 Fluorospectrometer, exciting with the UV LED, and monitoring emission at 509 nm, as directed by the manufacturer. Replicate experiments were performed on separate days. Digital photographs of strain NJH371 (FIG. 4B) were acquired with a tripod mounted Canon Powershot A630 automatic camera, using either daylight or a hand-held UV lamp (366 nm) as the light source. Adobe Photoshop CS2 was utilized to isolate the green channel of the UV illuminated RGB image, as well as to scale the green channel intensity, maintaining a gamma of one, to maximize the dynamic display range.

$P_{xyl}$ urcA-mcherry Strain.

The genomic region containing urcA was amplified from Caulobacter CB15N genomic DNA with KOD Hot Start DNA polymerase using oligos NJH204 and NJH205, as described above except the extension time was 2 min 30 sec. The PCR product was then reamplified using oligos NJH200 and NJH213, as described above except the extension time was 30 sec. This second PCR product containing urcA was then digested with NdeI and EcoRI.

An AgeI/BsrGI fragment containing mcherry was amplified from pRSET-B mcherry using oligos NJH25 and NJH26, as described above except the extension time was 1 min, digested with AgeI and BsrGI, ligated into similarly digested pMT383, and the sequence of resulting plasmid, pNJH15, was confirmed by primer extension sequencing using oligos NJH25 and NJH26. Plasmid pNJH15 was digested with EcoRI and BsrGI to yield a 750 bp EcoRI/BsrGI fragment containing mcherry, which was isolated by gel electrophoresis.

Plasmid pMT397 was sequentially digested with SmaI and then EcoRI, to yield an 800 bp EcoRI/SmaI fragment containing eyfp, which was isolated by gel electrophoresis, and then ligated into the vector backbone of similarly digested pNJH153, to yield pNJH156. Plasmid pNJH156 was digested with NdeI/BsrGI, and the vector backbone was ligated with the NdeI/EcoRI fragment containing urcA (see above) and the EcoRI/BsrGI fragment containing mcherry (see above) (triple ligation), and the sequence of resulting plasmid, pNJH169, was confirmed by primer extension sequencing using oligo NJH210. Caulobacter crescentus CB15N was transformed with plasmid pNJH169 by electroporation as previously described to yield the Pxyl UrcA-mCherry strain NJH300. Strain NJH300 was grown overnight at 28° C. in M2G media to an $OD_{660\,nm}$ of about 0.3, induced with 0.3% xylose for 3 hours at 28° C. and immobilized onto 1.0% agar in M2G before imaging with phase and epifluorescent deconvolution microscopy with a Leica DM6000 microscope using ImagePro Plus v6.0 (with embedded SharpStack Plus) software.

DNA Oligos Used in this Study

Underlined portions indicate endonuclease recognition sites (NJH25: AgeI; NJH26: BsrGI; NJH120: BglII; NJH121: KpnI; NJH122: NcoI; NJH123: NheI; NJH144: AscI; NJH200: NdeI; NJH213: EcoRI; NJH238: NcoI; NJH239: SpeI) or sticky single-stranded ends of annealed oligo pairs that are complimentary to digested DNA (NJH246/247: NcoI compatible ends; NJH248/249: NcoI compatible ends). The character "P" at the 5' end of the oligo sequence indicates 5' phosphorylation.

| SEQ ID NO: 1 | NJH120 | cgagaTCTggccggccgcacgcaagggc aga |
|---|---|---|
| SEQ ID NO: 2 | NJH121 | ggcgacggGTACcaggctcatgatgaac ttgcgcatttga |
| SEQ ID NO: 3 | NJH122 | catcatcaCcGGTCGGCtACCatggcAa gcaaaggagaagaa |
| SEQ ID NO: 4 | NJH123 | aagTttcgCTAGcCtatttgtagagctc atccatgccatgtg |
| SEQ ID NO: 5 | NJH144 | gagacgcggcGCgccgcacgcaagggca gatcatcggcct |
| SEQ ID NO: 6 | NJH155 | aagcaacggcccggagggtgg |
| SEQ ID NO: 7 | NJH156 | ccgggctgcaggaattcgatatcaagc |

-continued

| SEQ ID NO: 8 | NJH236 | gaaaactacctgttccGtggccaacact tgtcacta |
| --- | --- | --- |
| SEQ ID NO: 9 | NJH237 | tagtgacaagtgttggccaCggaacagg tagtttt |
| SEQ ID NO: 10 | NJH238 | atgatAaCcAtgGTcatttgaagtatcc ctctggctgg |
| SEQ ID NO: 11 | NJH239 | cccccggActAGTgctagcctatttgta gagctcatcc |
| SEQ ID NO: 12 | NJH240 | tcggcagaatgcttaatgaattacaaca |
| SEQ ID NO: 13 | NJH241 | ccataagagaaagtagtgacaagtgttg |
| SEQ ID NO: 14 | NJH242 | gagcgcgcgtaatacgactcactatagg |
| SEQ ID NO: 15 | NJH243 | gcgcgtaatacgactcacta |
| SEQ ID NO: 16 | NJH244 | gcacagatgcgtaaggagaa |
| SEQ ID NO: 17 | NJH246 | PcatgggggttctcatcatcatcatcatcatgG |
| SEQ ID NO: 18 | NJH247 | PcatgCcatgatgatgatgatgatgagaaccccc |
| SEQ ID NO: 19 | NJH248 | PcatggtcacacaggaaacagG |
| SEQ ID NO: 20 | NJH249 | PcatgCctgttttcctgtgtgac |
| SEQ ID NO: 21 | NJH25 | gggatccaccggtagccaccatggtaag caagggcgagga |
| SEQ ID NO: 22 | NJH26 | gaattcttacttgtacagctcgtccatg ccgc |
| SEQ ID NO: 23 | NJH200 | gatacttcaTatgcgcaagttcatcatg agcctgaccacc |
| SEQ ID NO: 24 | NJH204 | gaactgtggacaccggaatg |
| SEQ ID NO: 25 | NJH205 | tcgccttcgccaagctgaac |
| SEQ ID NO: 26 | NJH213 | gtAgcTtgaattctctgcgcggcgagct cgaccgtcgt |

Plasmids Used in this Study.

| Plasmid | Description | Reference |
| --- | --- | --- |
| pPR9TT | translational fusion LacZ reporter vector | |
| pNJH123 | pPR9TT-PurcA__LacZ reporter vector | This study |
| pBAD-GFP | prokaryotic GFPuv expression vector | |
| pRVYFP-2 | low copy expression vector | |
| pNJH193 | low copy PurcA__GFPuv reporter vector | This study |
| pNJH198 | low copy PurcA__His$_6$GFPuv reporter vector | This study |
| pRKLac290 | transcriptional fusion LacZ reporter vector | |
| pNJH200 | low copy PurcA__RBS__His$_6$GFPuv reporter vector | This study |
| pBVMCS-2 | high copy expression vector | |
| pNJH201 | high copy PurcA__RBS__His$_6$GFPuv reporter vector | This study |
| pNJH153 | pX31-P$_{xyl}$ gfpuv expression vector | This study |
| pRSET-B-mCherry | mCherry expression vector | Shaner, et al. 2004. Nat Biotechnol 22: 1567-72 |
| pMT383 | pP$_{van}$-ftsZ-eyfp expression integration vector | Thanbichler and Shapiro 2006 Cell 126: 147-62 |
| pNJH15 | pP$_{van}$-ftsZ-mcherry expression integration vector | This study |
| pMT397 | low copy pP$_{van}$-MCS-eYFP expression vector | |
| pNJH156 | pX31-P$_{xyl}$ gfpuv (-eyfp) expression vector | This study |
| pNJH169 | pX31-P$_{xyl}$ urcA-mcherry expression vector | This study |

Strains Used in this Study.

| Strain | Description | Reference |
| --- | --- | --- |
| LS4358 | Caulobacter CB15N Δcc1634 | |
| NJH199 | Caulobacter CB15N Δcc1634 pNJH123 | This study |
| LS101 | Caulobacter CB15N | (Evinger, M., and N. Agabian. 1977 J Bacteriol 132: 294-301) |
| NJH371 | Caulobacter CB15N pNJH201 | This study |

A custom designed Affymetrix array of the C. crescentus genome, CauloHI1, used to quantitate transcript levels upon exposure of Caulobacter to heavy metals, revealed that several genes were specifically upregulated upon exposure to uranyl nitrate. One of these genes is induced 27.5 fold under uranium stress, but is not upregulated in response to other heavy metals in the test screen. We have named this gene urcA, for uranium response in Caulobacter A and selected the urcA promoter as a candidate to drive uranium reporter constructs. Results from the microarray experiments localized the urcA+1 transcriptional start site to within a 10 base pair window (FIG. 1A). CC3302Hypp_x_at probe 3 is the most upstream probe in the Affymetrix array to match the urcA transcript, placing its +1 site approximately 5 to 15 base pairs upstream from the end of the immediately adjacent probe 2 (chromosomal position 3552896). A uranium-inducible promoter sequence motif, present within the promoter regions of eleven Caulobacter genes, has been identified. The urcA promoter contains two matches to this uranium-specific m__5 motif, located 107 and 55 base pairs upstream of the putative +1 site (FIG. 1A,C). The urcA transcript overlaps the opposing strand of gene cc3302 of the original annotation of the Caulobacter genome, but the revised Glimmer and GeneMark annotations of the Caulobacter genome now identify urcA as the true ORF (spanning from chromosomal position 3552927 to 3553280 on the positive strand), dispensing with the originally annotated cc3302 gene. The urcA gene is not essential for viability, and is not conserved among other α-proteobacteria.

Figure 2:
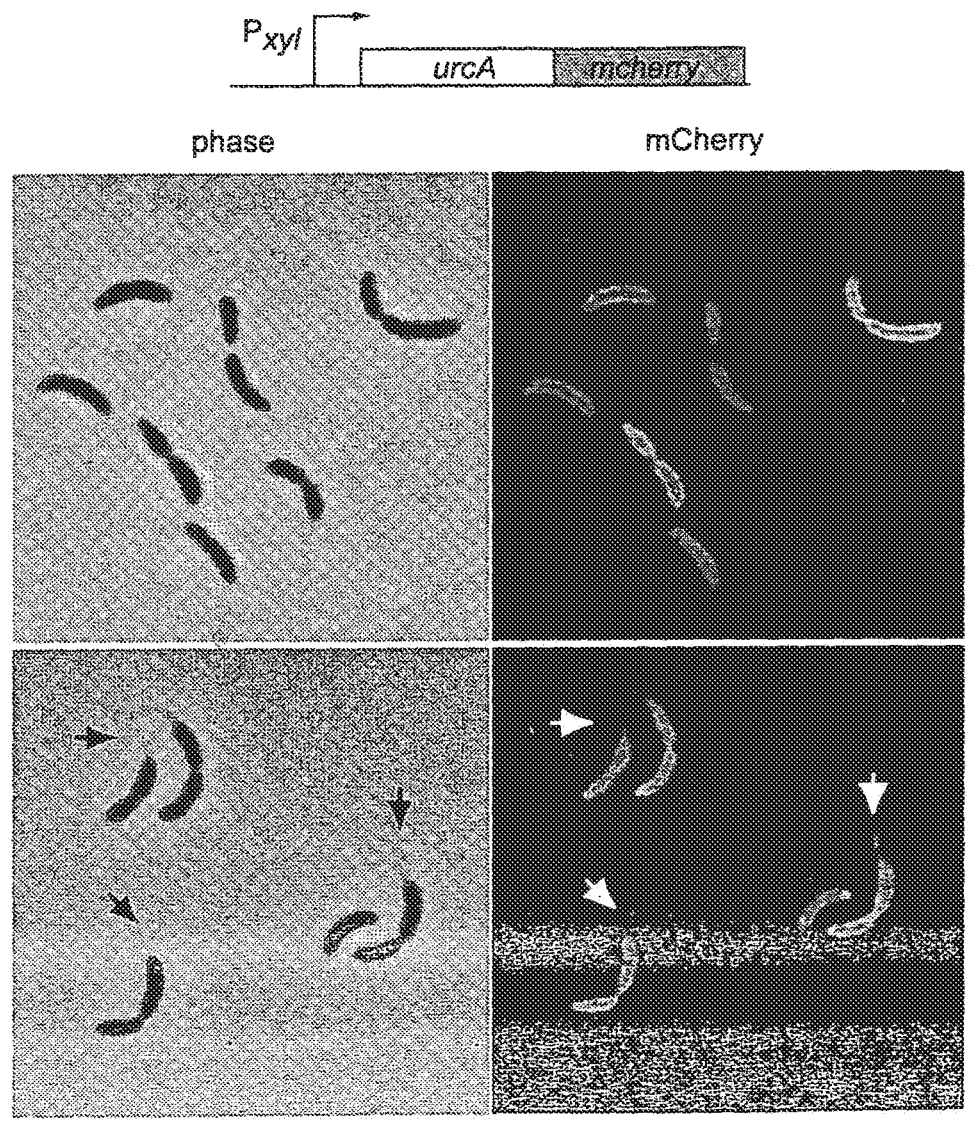
FIG. 2. UrcA-mCherry localization. Strain NJH300 was induced with 0.3% xylose for 3 hours and imaged with deconvolution microscopy. Phase contrast and epifluorescence images are shown. Arrows point to representative cell stalks visible within both phase contrast and epifluorescence images.

The urcA gene encodes a predicted 12.7 kD protein. The signal sequence prediction tool SignalP predicts with near 100% certainty that UrcA contains an N-terminal signal sequence whose most likely cleavage site is located between residues 30 and 31, and the prokaryotic subcellular protein localization tool SubLoc predicts with 96% expected accuracy that UrcA is a periplasmic protein. To experimentally test the bioinformatic prediction of UrcA's periplasmic localization, we constructed a xylose inducible UrcA-mCherry fusion. After xylose induction, the P$_{xyl}$ urcA-mcherry strain was imaged with deconvolution microscopy (FIG. 2). The fluorescence images are consistent with UrcA localizing to the cell periphery and to the cell stalk.

Figure 3:
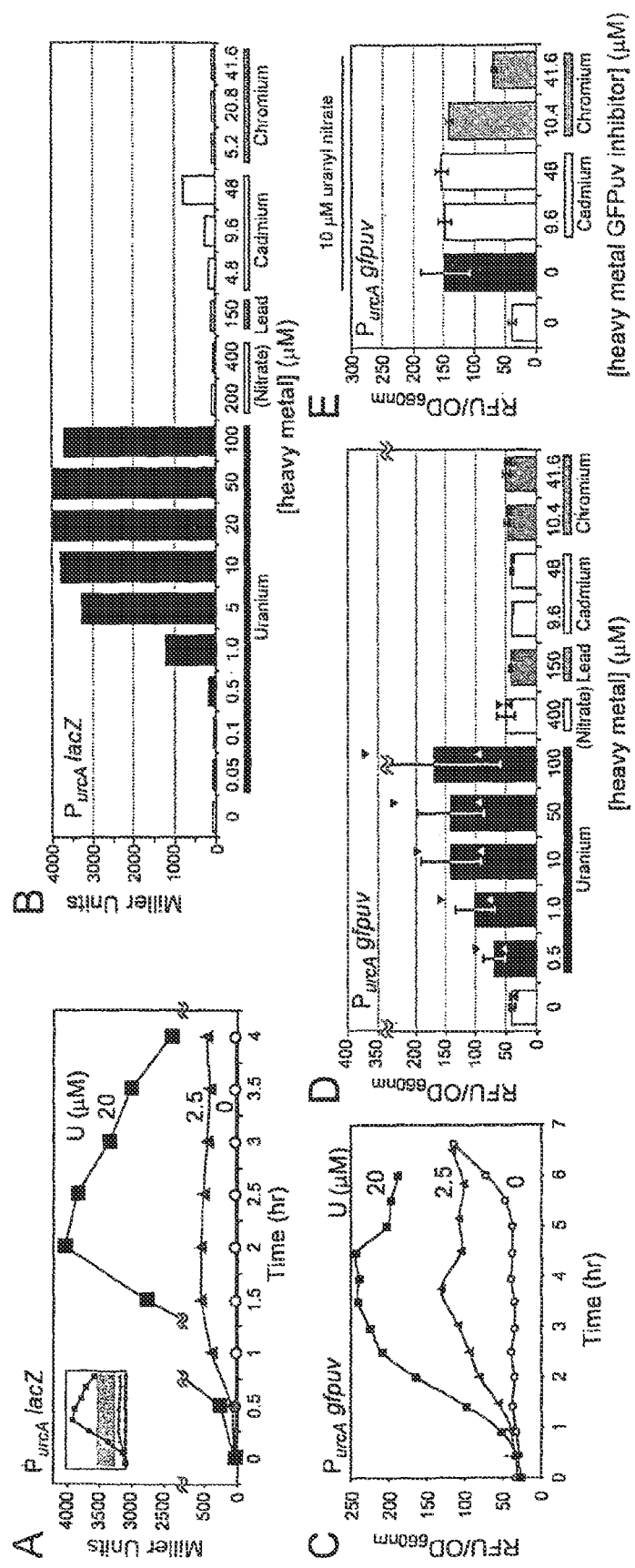
FIG. 3. $P_{urcA}$ lacZ and $P_{urcA}$ gfpuv reporter kinetics, sensitivity and specificity. (A) Time course of strain NJH199 β-ga-lactosidase activity in liquid culture after induction with uranyl nitrate. Midsection of the plot, shown in the grey region of the inset, has been removed. (B). Strain NJH199 β-galactosidase activity after two hours heavy metal exposure. (C) Time course of GFPuv fluorescence (relative fluorescence units, RFU, divided by culture $OD_{660\ nm}$) for strain NJH371 ($P_{urcA}$ gfpuv), after induction with uranyl nitrate. (D) Strain NJH371 GFPuv fluorescence after four hours heavy metal exposure. Error bars indicate one standard deviation from the mean; triangles indicate the maximum and minimum observed fluorescence values. Aggregate results from (N=7), uranyl and mock treatments; or (N=3) replicate experiments. (E) Inhibitory effect of high concentrations of chromium on GFPuv reporter function. Strain NJH371 was induced with 10 μM uranyl nitrate (indicated by the horizontal line above), with the absence or presence of cadmium or chromium, for four hours before assaying GFPuv fluorescence. Aggregate results from (N=5), 10 μM uranyl nitrate alone; or (N=3) replicate experiments.

To determine if the urcA promoter could be a candidate uranium biosensor, we constructed a plasmid-borne LacZ fusion reporter, containing 1 kb of the promoter region upstream of the urcA start ATG codon, through the first 8 amino acids of UrcA fused to LacZ to create strain NJH199 (FIG. 1B). The resulting $P_{urcA}$ lacZ reporter strain was exposed to 0, 2.5 or 20 µM uranyl, and the resulting kinetics of β-galactosidase activity was assayed in liquid culture (FIG. 3A). The $P_{urcA}$ lacZ strain is able to detect the presence of 2.5 µM uranyl, and maximal β-galactosidase activity occurs by 2 hours of exposure to either 2.5 or 20 µM uranyl nitrate. To test the sensitivity and specificity of the reporter, the $P_{urcA}$ lacZ strain was exposed to a panel of heavy metals for two hours, and then assayed for β-galactosidase activity (FIG. 3B). The $P_{urcA}$ lacZ reporter's detection limit for uranyl after 2 hours exposure is about 1.0 µM. The maximum signal increase of the $P_{urcA}$ lacZ reporter is 65-fold over background at 20 µM uranyl. The $P_{urcA}$ lacZ reporter is not stimulated by the presence of lead (150 µM) or chromium (41.6 µM), but shows cross sensitivity to cadmium at 48 µM. In addition to the panel of heavy metals, the $P_{urcA}$ lacZ reporter response to nitrate was assayed as a negative control, to ensure that the nitrate component of uranyl nitrate salt does not contribute to $P_{urcA}$ lacZ reporter activity.

After success with the $P_{urcA}$ lacZ reporter, we constructed a reporter strain (NJH371) in which plasmid-borne $P_{urcA}$ drives the expression of UV-excitable GFP fluorescence. The $P_{urcA}$ gfpuv reporter construct is shown in FIG. 1B. The time course of GFPuv signal kinetics for $P_{urcA}$ gfpuv, after induction with uranyl nitrate is shown in FIG. 3C. Fluorescence activity for the $P_{urcA}$ gfpuv reporter strain reaches a maximum between 3 and 4 hours of exposure to uranyl, but half the maximum activity is achieved after about 2 hours. It should be noted that as the $P_{urcA}$ gfpuv reporter strain reaches high cell density at 6.5 hours (>0.9 $OD_{660\ nm}$), entering stationary phase in the absence of uranium, the basal activity level of $P_{urcA}$ gfpuv begins to increase. This result cautions against using high density cultures of the $P_{urcA}$ gfpuv reporter strain, which could lead to false positives when probing for the presence of uranium.

The $P_{urcA}$ gfpuv reporter strain was exposed to a panel of heavy metals for four hours, and then assayed for fluorescence activity (FIG. 3D). The $P_{urcA}$ gfpuv reporter exhibits specificity for uranium, with little cross specificity with nitrate (<400 µM), lead (<150 µM), cadmium (<48 µM) or chromium (<41.6 µM). The $P_{urcA}$ gfpuv reporter's detection limit for uranyl after 4 hours exposure is around 0.5 µM. The mean signal increase of the $P_{urcA}$ gfpuv reporter is 4.2-fold over background at 100 µM uranyl. Despite sizeable standard deviations in reporter fluorescence activity, it should be pointed out that the minimum measured activities (N=7) of the reporter for uranyl concentrations above 0.5 µM are all greater than the maximum measured (N=3) for nitrate, lead, cadmium or chromium. Interestingly, we did not observe low level stimulation of the GFPuv reporter by cadmium, contrasting with the LacZ reporter results (FIG. 3B). An inhibitory affect of 41.6 µM chromium on GFPuv activity is observed for the $P_{urcA}$ gfpuv reporter (FIG. 3E), but cadmium levels less than 48 µM do not appear to significantly affect $P_{urcA}$ gfpuv reporter activity in the presence of 10 µM uranyl.

Figure 4:
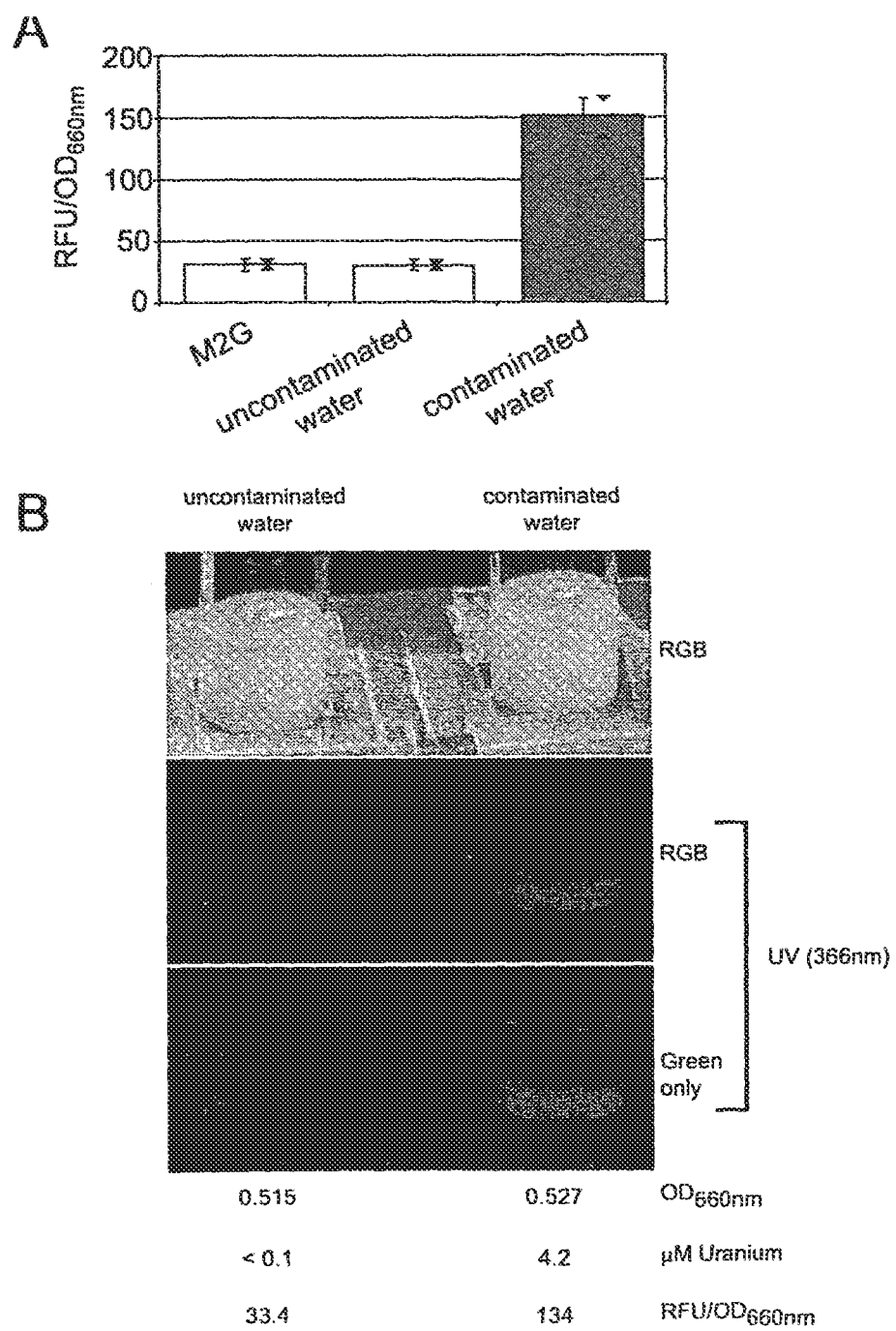
FIG. 4. $P_{urcA}$ gfpuv reporter detection of uranium contaminated ground water. (A) Strain NJH371 GFPuv fluorescence was assayed after four hours exposure to uranium contaminated (4.2 μM) or uncontaminated (<0.1 μM) Oak Ridge Field Research Center water samples; M2G minimal media shown as a negative control. Error bars and triangles as in FIG. 3D. Aggregate results from (N=4) experiments. (B) Cultures of strain NJH371, illuminated with either daylight or a hand held UV lamp, were photographed after four hours exposure to uranium contaminated or uncontaminated water samples. The isolated green channel of the UV illuminated RGB (red, green, and blue channels) image, as well as culture $OD_{660\ nm}$ and GFPuv fluorescence measurements for the photographed cultures, are presented below.

FIG. 4 demonstrates that the $P_{urcA}$ gfpuv strain discriminates uranium contaminated (4.2 µM) from uncontaminated (<0.1 µM) ground water samples collected at the Oak Ridge Field Research Center. Adding 50 µM uranyl nitrate to the uncontaminated water sample yielded comparable photoemission. Using a hand held UV lamp as the light source, the naked eye alone is sufficient to distinguish $P_{urcA}$ gfpuv reporter strain cultures exposed to the contaminated water (4.2 µM uranium) from those exposed to the uncontaminated water (FIG. 4B), although filtering out the blue region of the spectrum (as shown by isolating the green channel of the RGB image) facilitates the discrimination. This key result demonstrates that the $P_{urcA}$ gfpuv reporter strain can be used to detect the presence of uranium contamination in real-world water samples, that the reporter's output can be successfully monitored with the naked eye without resorting to a fluorimeter, and that the chemical composition background of the water samples tested do not induce false positive or negative results.

In the work presented here, we have constructed a whole cell uranium biosensor that can report the presence of micro molar amounts of the uranyl cation in situ with nothing other than a hand held UV lamp. To accomplish this, we have utilized a reporter construct that places GFPuv under the control of the promoter of the *Caulobacter* gene, urcA, that is strongly upregulated upon exposure to uranium. A promoter motif was identified in eleven *Caulobacter* genes that are induced in response to uranyl nitrate. The urcA promoter contains a tandem repeat of this uranium response motif, m_5, which may explain why urcA is so much more strongly upregulated under uranium stress than any other *Caulobacter* gene. The m_5 uranium response motif is similar to the cell cycle regulation promoter motif cc_1, which appears to be stress-induced. As the optical density of a $P_{urcA}$ gfpuv reporter strain culture begins to exceed an $OD_{660\ nm}$ of about 0.92, at 6.5 hours, the fluorescence activity becomes quantitatively comparable to the reporter's activity output after four hours exposure to 2.5 µM uranyl (FIG. 3C). This increase of the basal activity level of the $P_{urcA}$ GFPuv reporter upon entry into high cell density is consistent with UrcA's role in stress response.

The $P_{urcA}$ gfpuv reporter strain is able to discriminate micromolar levels of uranium-contaminated from uncontaminated ground water samples acquired from the Oak Ridge Field Research Center, demonstrating that this reporter can successfully applied to real-world samples. High levels of contaminating chromium (41.6 µM), but not cadmium, decreased the uranyl-induced GFPuv fluorescence activity of the $P_{urcA}$ gfpuv reporter. The maximum signal of the $P_{urcA}$ gfpuv reporter is achieved after 3 to 4 hours of uranium exposure, but the assay time could confidently be reduced to 2 hours at the expense of increasing the detection limit from about 0.5 to 1.0 µM uranyl. Other uranium detection methods have shorter measurement times (about 8 minutes for the catalytic DNA beacon biosensor), but the $P_{urcA}$ gfpuv reporter strain does not require any preliminary sample processing. The 0.5 µM uranyl detection limit of the $P_{urcA}$ gfpuv reporter corresponds well with the EPA maximum contaminant level guideline of 0.13 µM uranium. The $P_{urcA}$ gfpuv reporter strain differs from more sensitive uranium detection methodologies in that it provides signal only for toxic levels of bioavailable uranium contamination. Presumably, the detection limit of the urcA promoter has been tuned to coincide with the uranyl concentration above which uranium stress is toxic to *Caulobacter*. The $P_{urcA}$ gfpuv reporter strain additionally differs from other uranium detection methodologies in that it requires minimal equipment and sample processing, and operates at ambient temperatures.

Development of the $P_{urcA}$ gfpuv reporter includes field-ready application, spraying the strain directly upon soil, ground water, or industrial surfaces. Freeze-drying whole cell bacterial cadmium biosensors has been shown to only moderately affect performance, and reconstituting the $P_{urcA}$ gfpuv reporter strain from a lyophilized powder can greatly enhance its on-demand usability in the field. In conjunction with bioremediation efforts, the $P_{urcA}$ gfpuv reporter can complement analytical uranium detection methodologies by rapidly screening many locations in parallel for toxic levels of bio-available uranium contamination.

It is understood that the examples and embodiments described herein are for illustrative purposes only and that various modifications or changes in light thereof will be suggested to persons skilled in the art and are to be included within the spirit and purview of this application and scope of the appended claims.

We claim:

1. A genetically modified bacterial cell comprising a polynucleotide sequence encoding a reporter protein, wherein the polynucleotide sequence is operably linked to a heavy metal regulated promoter, wherein said heavy metal regulated promoter is a promoter sequence of *Caulobacter* protein CC3302 (SEQ ID NO: 30).

2. The bacterial cell according to claim 1, wherein said cell is *Caulobacter crescentus*.

3. The bacterial cell according to claim 1, wherein said polynucleotide sequence encoding a reporter protein operably linked to a heavy metal regulated promoter is provided on a plasmid vector.

4. The bacterial cell according to claim 1, wherein said reporter protein is a green fluorescent protein (GFP).

5. The bacterial cell according to claim 1, wherein said heavy metal is uranium.

6. A method of detecting the presence of a heavy metal in a sample, the method comprising:
    contacting said sample with a bacterial cell according to claim 1
       incubating for a period of time sufficient to upregulate expression from said heavy metal regulated promoter, and
    detecting the presence of said reporter protein.

7. The method according to claim 6, wherein said detection is by naked eye.

8. The method according to claim 6 wherein said detection is by fluorimeter.

9. The genetically modified bacterial cell of claim 4, wherein the promoter comprises at least one uranium specific promoter motif sequence.

10. A genetically modified bacterial cell comprising a polynucleotide sequence encoding a reporter protein, wherein the polynucleotide sequence is operably linked to a heavy metal regulated promoter, wherein the sequence of said heavy metal regulated promoter is at least 90% identical to SEQ ID NO: 30 or fragments thereof.

11. The bacterial cell of claim 10, wherein the promoter sequence contains at least 50 nucleotides.

12. The bacterial cell of claim 10, wherein the promoter sequence contains at least 100 nucleotides.

13. The bacterial cell of claim 10, wherein the nucleotides 52-79 and 104-131 are present in the promoter that is at least 90% identical to SEQ ID NO: 30.

14. A genetically modified bacterial cell comprising a polynucleotide sequence encoding a reporter protein, wherein the polynucleotide sequence is operably linked to a heavy metal regulated promoter, wherein said heavy metal regulated promoter comprises a first uranium specific promoter motif sequence and a second uranium specific promoter sequence, wherein the first uranium specific motif sequence comprises SEQ ID NO: 28 and wherein the second uranium specific motif sequence comprises SEQ ID NO: 29.

15. The bacterial cell of claim 14, wherein the promoter sequence contains at least 50 nucleotides.

16. The bacterial cell of claim 14, wherein the promoter sequence contains at least 100 nucleotides.

17. The bacterial cell according to claim 1, wherein said bacterial cell is a *Caulobacter* cell.

18. The bacterial cell according to claim 17, wherein said polynucleotide sequence encoding a reporter protein operably linked to a heavy metal regulated promoter is integrated into the chromosome of said *Caulobacter*.

* * * * *

SEQUENCE LISTING

```
<160> NUMBER OF SEQ ID NOS: 30

<210> SEQ ID NO 1
<211> LENGTH: 31
<212> TYPE: DNA
<213> ORGANISM: Artificial Sequence
<220> FEATURE:
<223> OTHER INFORMATION: NJH120 oligonucleotide

<400> SEQUENCE: 1
cgagatctgg ccggccgcac gcaagggcag a                                      31

<210> SEQ ID NO 2
<211> LENGTH: 40
<212> TYPE: DNA
<213> ORGANISM: Artificial Sequence
<220> FEATURE:
<223> OTHER INFORMATION: NJH121oligonucleotide

<400> SEQUENCE: 2
ggcgacgggt accaggctca tgatgaactt gcgcatttga                             40

<210> SEQ ID NO 3
<211> LENGTH: 42
<212> TYPE: DNA
<213> ORGANISM: Artificial Sequence
<220> FEATURE:
<223> OTHER INFORMATION: NJH122 Oligonucleotide

<400> SEQUENCE: 3
catcatcacc ggtcggctac catggcaagc aaaggagaag aa                          42

<210> SEQ ID NO 4
<211> LENGTH: 42
<212> TYPE: DNA
<213> ORGANISM: Artificial Sequence
<220> FEATURE:
<223> OTHER INFORMATION: NJH123 Oligonucloetide

<400> SEQUENCE: 4
aagtttcgct agcctatttg tagagctcat ccatgccatg tg                          42

<210> SEQ ID NO 5
<211> LENGTH: 40
<212> TYPE: DNA
<213> ORGANISM: Artificial Sequence
<220> FEATURE:
<223> OTHER INFORMATION: NJH144 Oligonucleotide

<400> SEQUENCE: 5
gagacgcggc gcgccgcacg caagggcaga tcatcggcct                             40

<210> SEQ ID NO 6
```

```
<211> LENGTH: 21
<212> TYPE: DNA
<213> ORGANISM: Artificial Sequence
<220> FEATURE:
<223> OTHER INFORMATION: NJH155 Oligonucleotide

<400> SEQUENCE: 6
aagcaacggc ccggagggtg g                                              21

<210> SEQ ID NO 7
<211> LENGTH: 27
<212> TYPE: DNA
<213> ORGANISM: Artificial Sequence
<220> FEATURE:
<223> OTHER INFORMATION: NJH156 Oligonucleotide

<400> SEQUENCE: 7
ccgggctgca ggaattcgat atcaagc                                        27

<210> SEQ ID NO 8
<211> LENGTH: 36
<212> TYPE: DNA
<213> ORGANISM: Artificial Sequence
<220> FEATURE:
<223> OTHER INFORMATION: NJH236 Oligonucleotide

<400> SEQUENCE: 8
gaaaactacc tgttccgtgg ccaacacttg tcacta                              36

<210> SEQ ID NO 9
<211> LENGTH: 35
<212> TYPE: DNA
<213> ORGANISM: Artificial Sequence
<220> FEATURE:
<223> OTHER INFORMATION: NJH237 Oligonucleotide

<400> SEQUENCE: 9
tagtgacaag tgttggccac ggaacaggta gtttt                               35

<210> SEQ ID NO 10
<211> LENGTH: 38
<212> TYPE: DNA
<213> ORGANISM: Artificial Sequence
<220> FEATURE:
<223> OTHER INFORMATION: NJH238 Oligocnucloetide

<400> SEQUENCE: 10
atgataacca tggtcatttg aagtatccct ctggctgg                            38

<210> SEQ ID NO 11
<211> LENGTH: 38
<212> TYPE: DNA
<213> ORGANISM: Artificial Sequence
<220> FEATURE:
<223> OTHER INFORMATION: NJH239 oligonucleotide

<400> SEQUENCE: 11
cccccggact agtgctagcc tatttgtaga gctcatcc                            38

<210> SEQ ID NO 12
<211> LENGTH: 28
<212> TYPE: DNA
<213> ORGANISM: Artificial Sequence
<220> FEATURE:
<223> OTHER INFORMATION: NJH240 oligonucleotide

<400> SEQUENCE: 12
```

```
tcggcagaat gcttaatgaa ttacaaca                                          28

<210> SEQ ID NO 13
<211> LENGTH: 28
<212> TYPE: DNA
<213> ORGANISM: Artificial Sequence
<220> FEATURE:
<223> OTHER INFORMATION: NJH241 oligonucleotide

<400> SEQUENCE: 13
ccataagaga aagtagtgac aagtgttg                                          28

<210> SEQ ID NO 14
<211> LENGTH: 28
<212> TYPE: DNA
<213> ORGANISM: Artificial Sequence
<220> FEATURE:
<223> OTHER INFORMATION: NJH242 oligonucleotide

<400> SEQUENCE: 14
gagcgcgcgt aatacgactc actatagg                                          28

<210> SEQ ID NO 15
<211> LENGTH: 20
<212> TYPE: DNA
<213> ORGANISM: Artificial Sequence
<220> FEATURE:
<223> OTHER INFORMATION: NJH243 oligonucleotide

<400> SEQUENCE: 15
gcgcgtaata cgactcacta                                                   20

<210> SEQ ID NO 16
<211> LENGTH: 20
<212> TYPE: DNA
<213> ORGANISM: Artificial Sequence
<220> FEATURE:
<223> OTHER INFORMATION: NJH244 oligonucelotide

<400> SEQUENCE: 16
gcacagatgc gtaaggagaa                                                   20

<210> SEQ ID NO 17
<211> LENGTH: 33
<212> TYPE: DNA
<213> ORGANISM: Artificial Sequence
<220> FEATURE:
<223> OTHER INFORMATION: NJH246 oligonucleotide

<400> SEQUENCE: 17 catgggggt tctcatcatc atcatcatca tgg                                     33

<210> SEQ ID NO 18
<211> LENGTH: 33
<212> TYPE: DNA
<213> ORGANISM: Artificial Sequence
<220> FEATURE:
<223> OTHER INFORMATION: NJH247 oligonucleotide

<400> SEQUENCE: 18
catgccatga tgatgatgat gatgagaacc ccc                                    33

<210> SEQ ID NO 19
<211> LENGTH: 21
<212> TYPE: DNA
<213> ORGANISM: Artificial Sequence
<220> FEATURE:
```

<223> OTHER INFORMATION: NJH248

<400> SEQUENCE: 19
catggtcaca caggaaacag g                                         21

<210> SEQ ID NO 20
<211> LENGTH: 21
<212> TYPE: DNA
<213> ORGANISM: Artificial Sequence
<220> FEATURE:
<223> OTHER INFORMATION: NJH249 oligonucleotide

<400> SEQUENCE: 20
catgcctgtt tcctgtgtga c                                         21

<210> SEQ ID NO 21
<211> LENGTH: 40
<212> TYPE: DNA
<213> ORGANISM: Artificial Sequence
<220> FEATURE:
<223> OTHER INFORMATION: NJH25 oligonucleotide

<400> SEQUENCE: 21
gggatccacc ggtagccacc atggtaagca agggcgagga                     40

<210> SEQ ID NO 22
<211> LENGTH: 32
<212> TYPE: DNA
<213> ORGANISM: Artificial Sequence
<220> FEATURE:
<223> OTHER INFORMATION: NJH26 oligonucleotide

<400> SEQUENCE: 22
gaattcttac ttgtacagct cgtccatgcc gc                             32

<210> SEQ ID NO 23
<211> LENGTH: 40
<212> TYPE: DNA
<213> ORGANISM: Artificial Sequence
<220> FEATURE:
<223> OTHER INFORMATION: NJH200 oligoncletide

<400> SEQUENCE: 23
gatacttcat atgcgcaagt tcatcatgag cctgaccacc                     40

<210> SEQ ID NO 24
<211> LENGTH: 20
<212> TYPE: DNA
<213> ORGANISM: Artificial Sequence
<220> FEATURE:
<223> OTHER INFORMATION: NJH204 oligonucleotide

<400> SEQUENCE: 24
gaactgtgga caccggaatg                                           20

<210> SEQ ID NO 25
<211> LENGTH: 20
<212> TYPE: DNA
<213> ORGANISM: Artificial Sequence
<220> FEATURE:
<223> OTHER INFORMATION: NJH205 oligonucleotide

<400> SEQUENCE: 25
tcgccttcgc caagctgaac                                           20

<210> SEQ ID NO 26

```
<211> LENGTH: 38
<212> TYPE: DNA
<213> ORGANISM: Artificial Sequence
<220> FEATURE:
<223> OTHER INFORMATION: NJH213 oligonucleotide

<400> SEQUENCE: 26
gtagcttgaa ttctctgcgc ggcgagctcg accgtcgt                              38

<210> SEQ ID NO 27
<211> LENGTH: 12497
<212> TYPE: DNA
<213> ORGANISM: Caulobacter crescentus

<400> SEQUENCE: 27
atgcccacca caagtcgcga gcgatcagcg tttttcgaac cgtccgacat ggtgaatttt      60
cgtccgtctt gggagcaagc cgcgccacgt caagcggggc cgattgcaat catatgtgat    120
ctgacagcgc cgcgcagcgg gtgttcactt tcctctccac cagcaaggag ccagagccca    180
tggccatcga atcccgtatc cgcgagcttg gtcccgtca cgagaacctc gaccgcaaga     240
tccaggagga gaccaatcga cccggtagcg acggaacggc gctcagggag cttaagcggc    300
ggaaacttcg actgaaggaa gagatcgagg gcctcaaggc ccgaatgcac tagctgctag    360
aagcagccga aaaacgagag gccccgttcc ggcaaggaac ggggcctctg cttttttctgc   420 gacgcgccga ggcttagtcc tcgtcttcct cgtcgacata gcccgtggac ttgccgaaca    480
cgtcctcggc cttgagatcg ccgcggggcg cgcggaagtc ttcttcctct tcctcgacct    540
ccggctcgaa ctgaccggct tccgaagccg gacgcagggt cggatcttcc ggaacaatgc    600
ccttcttaag gtcgtccttg gccttcttct cggcggcctt cttgacgagg gcgtcgagct    660
ccagctgacc aaccaggccc agggtcaccg gatcgaccgg cttgatgttg gcggcgttcc    720
agtgcgtacg ggcgcgaacc tgctcgatcg tggccttggt ggtgcccagg atcttcgaga    780
tctgggcgtc ggtcacttcg gggtggtgac gcaggaacca ggcgatggcg tccggtcggt    840
cctggcggcg cgacacgggc gtgtaacgcg gggccttctt ggccggcttc agcagctcgg    900
cgtggcggct gaccagcgcc ttcatgcgat agtcgggatt ggcctgagcg cggtccagct    960
cttcgcgatt cagttgcccg ttgccgatcg ggtcggcgcc gcggatgtcg cgcgccactt   1020
cgccatcggc gatgccccgc acttccagcg ggtgcaggcc gcagaaatcg gcgatctgct   1080
cgaagctgag cgaggtgttg tccaccaacc agacggcggt cgccttgggc atcaggatgt   1140
cggacatgcg gtcctccaga aatgacgcg cccggccttt cggccgggcg ggttgttggt    1200
gaacgctata atccggttct cgtgaaaagg gaacggggga caagcagaga cagccattcc   1260
accgctcaaa tccacgcgct cattacttca gaccgtcagc acaaccttgc ctacgtgctc   1320
cccggcctcg aggtgagcat gcgccttggc cgcgtcagca agcgggaagg tcgcgtcgat   1380
gatcggcttc agcttgccgg ccgccaccca gggccagacg acgcgctcga cctcggcggc   1440
caggcgcgcc ttctcgtcgg ccgagcgggg gcgcagggtc gagccggtga tcaccgcccg   1500
cttctgcatg atcttcatca ccggaaccct cagcgtcgag ccgcccaggc tggcgatata   1560
gacaatgcgg ccgccgacat tgagggcgtc gaggttcttg tcgaaatagc tggcgccgac   1620
catgtcgagg atcacgtccg cgccgccggc ggccttcacg acctccgcga agtcctcggc   1680
cttggtgtcg acggcgatgt cggcgcccag ctcaagcgcc ttggccttct tgtcggcgcc   1740
gcgtcccgtg gcgatcacct ggcgccggc ggccttggcc atggcgatcg cagttgttcc    1800
gattccggac gttccaccgt gaaccagcag cgtctcgccg gccttcaagg cgccatgctc   1860
```

```
gaacacattg gcgaagacgg tgaagacggt ctcgggcagg gcggcggcct ggacgaggtc    1920
gagatccccc ggaatcggca gggcgtggcg ggcgtcgacc acggcgtact cggcgtatcc    1980
gccgccgccc aggagcgcgc aaaccttgtc gcccgccttc cagcggcccg cgccgaccac    2040
gacctcaccg gccacttcaa ggcccagggt ggcgggcgcg ccgggcggcg cgggtaaaa     2100 gcccatgcgc tgcaggaggt cggggcgatt cacgccggcc gccgccatct tgatcaggat    2160
ctcgccgggt cccggcgtgg gacgatccag ccgcgttgcg tgcagcgcct cgccggccc     2220 cttgccgcct tcgatcgcga tcgccgtcat cgtctcggcc atgccgggct ccttcgtggt    2280
gcttgccttg cggcctaggt aggcgtcaga tgtctgacgg aaaagggaga aaagccgatg    2340
ttcgaggagc ctgcagaagc ccgcgccttc ggcggacgcg ccttgaacga ggcgacccac    2400
gaggacctgg aagtctacgg cgtcgcggaa ctagaggagc gcatcgcggc tttgcaggcc    2460
gagatcgaac gtaccaaagc ccagctggcc aagaaaaagg cgggtcgcga tgcggccaat    2520
gcgctgtttg gtcgcctgga ctaacggttc ctttaaggtt tcggtgaggt tactggcggc    2580
ttaaggcggc tttcgcctct aggggttagt aggtcggttc gaaagggcgg gtcgcgaaac    2640
gggacggttg gctctggcac gggcgttgca gttcagtcgc caagcgagac gtcctcgcgg    2700
cctttcgaag gggcattgag tagctatgac cgaagtgaac gcgttcgcgg acacgccttg    2760
gcgcgctgga gtgatccagg atttcgcgcg atcggaactg ttcgaccgga cgttcgagga    2820
aggcatgcaa ctggtcgaag agaccgccgc ctatctcgac ggggccggac gccatgacag    2880
caaggtcctc tctcgcaacg ccgccctggg ctacgccacc gaaagcatgc gcctgaccac    2940
gcgcctgatg caggtcgcct cctggctttt ggtgcagcgc gccgtacgtg aaggcgagat    3000
gccgccggaa gccgcctgcg ctgaagccta tcgcctggcc gaagaggccc cggccgatgg    3060
tccggccgtc gaggaactgc cgtttggcct gatgaacctg ctgcagcgct ccgagcgcct    3120
gtacgagcgc gtccgccacc tggaccgccg catgtatgtc gagtcgccga acgaagaagc    3180
gccgcgtccg gttcagaacc agctcgatcg cttgacggcg cgttcggag gctaaggccc     3240 cgccccta ct tgccgaaccg catccgggcc agcgcggaga ccatctcgct ggccaggtcc    3300
atcggcttca ggcccgcctt ccacttctcg aacgccatca cgttgtcgat gcgcgcgtcc    3360
aggtgcgaca gcgccgaggc gcggcccgac gccatgtcga cggcgagggt ggagatcagg    3420
atccccgaca ggatcgcccg cttggagtag tggttctcgt cggtggcggt gtctccggcc    3480
cagcgccaga tggcgtccgc cgattcccag gtgagccgca acgccagcgc caggttagtc    3540
ggaaacgcca ggaaggccgc cagcggccgc agcacgtcgg cgttctcctg cgccgcgtcg    3600
agccgggcca ccacgccttc acggattcgc tggcggattt tcagagccgc gacatcaaag    3660
gcctgcaggc gcgccaaagc ggccgcgtca tggcgtcgcg acaaaagagc ggcgaggtcc    3720
cgtgcgccct caggcagcag cagctggcct tcagcctcgg aaagtcccgc cgcagacagg    3780
gcgcgactga caagtccgtt gttccagccg gccttgggcg cgaggcgcaa ggcctcgtcc    3840
agaacgcgct gttcagcctg atcggcccag tttgcgccag cttgatcgga agcttggccg    3900
gaggtgtcga cggtttcgct catgaatccg agtctacacc gtggtttagg ccgcgtcgcg    3960
catggacagc ggccgttggc tctgctatca gccccgcctc atcgcctgga agcacccctt    4020
ccggggcact ggttttattc gcccgcccgg cccctcaaga gggacttggg aattttggtc    4080
gggctgtcga atggagagat acccctggtc cagattttcg tccgcgacaa caacgtcgat    4140
caggccctga aggctctgaa gaagaagatg caacgcgaag gctcgttccg cgaaatgaag    4200
cggcacgtgc attatgaaaa gccgtcggaa aagcgcgcgc gccaaaaggc cgaagcggtc    4260
```

-continued

```
cgtcgcgccc gcaagctggc ccgcaagcgc gctcagcgcg aaggtctgct gccgatgccg   4320
aagaagccgg gccggtaaga cccgctcttc ttcacatcgc tgaagatttc gaaggccgcg   4380
cggcgatccg cgcggccttc gtcgttttcg gacctacccc gcctgcttgc gggcgatccg   4440
accgaccagg gtcttaaggt cgatcttccc ggtcgcagc gcgccgacgt ggaaggcgcg    4500
ggtcgagaac gccaccagcg cgacggtcgt cacgatcatc aagaccgtgg tgccgatgat   4560
ctggatcagc ggcgggtctc cggcgatccg caccggcatc aggaacggcg tgaagggcgg   4620
gatccaggac agggtcgaga gaatcggcga gtccggcgag cggatcgcct ggctcatgaa   4680
gatgatcggg atcgacatca ccaggatgat gggcccaagc agggtctggg cgtcgcgctg   4740
tgtctcgcag aacgcgccga cgccggcgaa aagcgcggcg tacatcaggt agccccgac    4800 gaggtaaacg ccgaaataga gcagcaggcc cttgcccagc agcacggcga cgagatcgcc   4860
ggcgaggccc ggcgcgaagt tgatcaaggc cacccaaccc gccatcgccc agacgcccat   4920
gaccgtcagg gtcagcccgg cgactcccag gatcttgccg cccatgatct cgggcaccga   4980
ggccgaggac agcaggacct ccaggatctt gctcgatttc tcctcgatca cgctgttcag   5040
caggatactg gccccggtca tgaccatcga ccacagcagg aagcccgcgg cgaggcccac   5100
aaaggtcggc agccgatccc gcagcgcgac cttcgcgccg gaggcggcct tgggtgagag   5160
gctgttgaag gtaggcttca gggcgtcggc ttcgctcagg gtctgggccg aaacgccggc   5220
tcgcgccagg gcccgctcgc gcatgatctc gctgaccgtc tggcgcagat cgccctccag   5280
caccggcgcg gcgaggttgc ggctccaaag atccagggtc acgtccgcgt cccgaccgct   5340
gacgatcagc accgaatcca gacgtttctc ggcgacctca cggcgggcga tcgcgccggc   5400
ttcggccggg gtcttggcgg ccagggcctg gccggggggc ggcagcacga ccgcgtcgac   5460
cttgggcgcc ttgaagcgcg cggcggctgt cggattgaag cgcgccaggg cttcgcgccc   5520
tgcggcgtcc ccgccttcaa gctgcgcctt ccggaccgct tcctgcgcct cgggtcccgc   5580
cgccgatagc gccgccgcgc gaagggctcg cgaagtggcg cgaccctggt cctcggccat   5640
ggccttggcg atggcgggcg cgaacgcctg atcggtcagg tcaataatag ccagccgctc   5700
gggcttggcg gacttcatca tcatcagcgg cgcggtgctg ctgatcccca tgaccagcgg   5760
caaggcgatg atcgacagcc agaagcccac ggtgcggaca taggccaggt actcccggcg   5820
cgcgatcttc agcagacggc tcatgcctgg cctcccgtca gcacaatgaa ggcgtcatgc   5880
agggtgggct ccttgagctc gaaccgcctg agcgaaagat cacgggcgaa agccgccttg   5940
agcgcatcct gccggtgct cgattccggc aaccgcgcca catgacgcca cccccatcc    6000 ggcaggggct ccgacgtcat ctcgccaaga ccgggcaagg cggcgacctc ctcggcggaa   6060
aggtcgcctt ccagcacgag cacccgcggc gccgcccgtc tcgcggtcac gacatcgccg   6120
tcgaacacct tctgcccccg cgccatcaag acgaccttgt cgcagagccg ctcggcgtgc   6180
tgcatcacgt gggtcgagaa cagcacggtg gcgccgcgcg ccgcgatctc gcggatcatc   6240
gtctccagcg cctgctggtt gaccgggtcc agccccgaga agggctcatc cagcaccacc   6300
agttccggtt cgtgcgccag cgccgacaga agctggacct tctgggccat gcccttggaa   6360
aggtccttga tcggccgctt catcgcaaag cccaggcctt gagcctccag cagggcctgg   6420
gcccgcttgc ggccctcggc ttcgggcacg ccccttcaagc cggcgaagaa ggcgatcgcg   6480
tcgatcggcg tcatgcgctt gtagaggccg cgctcctcgg ggagaaagcc gatccggtcg   6540
cgaacccttg tcgcgtcctc ggcgcccagc accgatatcc gccctgcgga gggcggcagc   6600
aggcccagga tcatgcggag cgtggatgtc ttgcccgcgc cgttggggcc caggaagccc   6660
```

-continued

```
gtgatccgcc cggcagggac ctcgaaactg acattccgca cggcatggaa gtcatcgtag    6720
gtcttgctga cccccttccag ggtgacggcg ctgaccatga dacggctccc gaatcgctcc    6780
tacgctctgg ttgtatcagc cctttccgcg agcgtcggcc acgaaggcga tggctcggac    6840
gatgcggtcg gcgaagcgtc gtccgatcag cagctggtgc gtcgccgcct ccacatggtc    6900
gacatagcca tgggtcgcgc ggcgggcggg ggcggcctgc atctcctttc gcagttcacg    6960
gcccgcgacg ggccctgcgg tcaccaccgc gatcggccag ttggggtcga actgcggctg    7020
ggcggcggcc tgggtcgagg cctcggccca caggcccacc tcctcggcgg ccgtgcggtt    7080
atgacggccg tcgcgaagg cccagctctt ctcggccttg gccgccggcg gcagatcgat    7140
cttgtcgccg aggcgcgtat ggatcagcgg cttgtagagc ccgatcgaag cgccgaaagc    7200
ggcccacttc gacacgcggg cgaaggtctt gatgaagccc tgcatcgacg gattgagcgc    7260
cgcttcaggc gtcgccgcat cgaccagaac cagacccgca atcttgtcgg ggtgacggcc    7320
ggcgtactcg cgcaggcgca ggccggccat cgagtgtccg accagaacgt agggacccgg    7380
ttcgccggac gcggccacca gcttctcgaa gtcggagacg atggccaggc catctcgagg    7440
actgggacct ttcggagaga agcccatgcc ggcgcggtca taggcgcacg atcgccagcc    7500
ttcggccgcg agcgcctcct gcgctgcgcc ccagtcggcg gcgaagccaa acgcaccggc    7560
ttcgagccag acgaccggtc gatcgctgct gggcccttca caaaccaggc gcagcacgcg    7620
ccccggctcg atctcgacca tcttgccgcg aatttgtggg gcgcccgtcg cgctcatcac    7680 gccgccgcc gcgatgtaga agatgaggac aagggcaagg cccgcgacgc cacgaccgac    7740
aaactggatc atggcgttca atgtaatggc ggttggcgaa cggtcgagac cgtcgatggt    7800
cggtttcgaa ttttaaatcg cggcttccgc cgaactcagc gccgtcgagg cggcgggcgc    7860
cggaactgtg gacaccggaa tggccgcctt ggcccgtccg gtcttcaaac gcgccaattg    7920
aaccttctcc ttggcgggct tggtcacgcc gggcggccag cgcagagacg tcgccttgtg    7980
gacttttcgc gagacgcggc cggccgcacg caagggcaga tcatcggcct cggcgaaggt    8040
tcgccccagg aagaagctgg gattgagcgg cttgtcaccc ttccggatct cgaaatggag    8100
atgcgagccc gaggaccgtc cggaattgcc gacgaaggcg acaatgtcgc ctcgccgcaa    8160
ataggcgccg cgcttcacgc tacgggcggg acgggccaga tgagcgtaca gggtcgacag    8220
accgcccttg tgcaccacaa ggacatagcg gccataggtg gcgctgaccc cggtggcctt    8280
tacgacgcca ggggccgcga ccttaacagc tgcgccggcg ggcgctgcga tatcaacgcc    8340
ctggtggagc cgaccgcttt cctcccacgg catctgtctc aagccgaagg gcgaattgat    8400
gacccgcccc ggcaagggtg cgtcaaagac gaaggccggg ggcggcgcct ggacctcggg    8460
ctccggtgcg ggttgcgcca ccgcagggat cgccgagctg gtcggcgcgc gcgcaatcca    8520
ctcgctcatc gcgaccgcgc cgttcaacgc gatcaccatc gcagcgatac ccagcatcga    8580
gaagagcgcg acgcgcaagt gctgcggcga tagcgccaag ctcatagaga ccaaaaccac    8640
ttcctcttcg acgcccggtc agtcgccagg accgcgtctg dacggttttg ctctcatact    8700
tgacctttcg ggatggtgaa tcgacggcgt gcatgaatgt cgcatcgggc ggaacggggc    8760
gtcgattaac cctttgcaaa ccatatactc aaacgaccca agcaatatgg tcacaaaaac    8820
ttcaaacatt acagactgtt tagaatatta agccccgta attctcttaa ttacgcgtca    8880
tgactgaggt gtaacgagac ttcgcgagaa cccgaatgta ccaatattc atcggcgcag    8940 cgaacagcgc ccagccagag ggatacttca aatgcgcaag ttcatcatga gcctgaccac    9000
cgtcgccacc ctgagcctcg ccgccgtgcc ggtcctgggc ctgacgcaag ccgccaacgc    9060
```

```
ctccgagagc gacccgcgcg tgagcattgc agtgtctgac ctgaacctgt cgaacccccgc    9120
ccaggccgcc ctgttcaagg cccgcgtcca gcaagccggc gagacgctct gccgcgcgaa    9180
gctgcgcaac aacaccctgg atatgtcgtt cggccagtgc cgcgtggaag tccaacgcga    9240
agccgagcgc caactgtcca agccccagcg caaggccctg atccaggcaa agcgggctac    9300
gacggtcgag ctcgccgcgc agtgatcgca caggcgaccg ccacacccca caccccgccc    9360
cgcgacagag gcctcaggta accctgaggc ctttgttttg cgcgcacgaa aaaggccccg    9420
gcgtcatcgc cggggccttc gtcgttccag gggcgaggcg tcaaagcccc ttcaggatcc    9480
cctcgaccat cttcttggcg tcgccgaaca acatcatcgt gttgtcgcgg aagaagagct    9540
cattctcgac cccggcatag cccgaggcca tgccgcgctt gacgaagagc actgtgcggg    9600
ccttctcgac gtccaggatc ggcatgccga agatggcgct ggtcgggtcg gtcttggccg    9660
ccgggttggt gacgtcattg gcgccgatca cgaaggcgac gtccgccgtc gagaactcgc    9720
tattgatgtc ctccagctcg aagacctcgt catagggcac attggcttcg gccagcagca    9780
cgttcatgtg gcccggcatc cggcccgcga cggggtggat ggcgtacttc acctcgacgc    9840
cttcttcctt cagcttgtcg gccatttcgc gcagggcgtg ctgggcctgg gacacggcca    9900
tgccgtagcc cgggacgatg atcaccttcg aggcgttctt catgatgaag gccgcgtcgt    9960
cggccgagcc ctgcttgacg gggcgggtct cgaccttacc gccgggaccg gccgcagccg   10020
catcagcgcc gaagccgccc aggatcaccg agacgaacga acggttcatg cccttacaca   10080
tgatgtagga caggatcgcg cccgacgaac cgaccagcgc gccggtgatg atcagggtgg   10140
tgttttccag cgtgaagccc agcgccgccg ccgcccaccc ggaatagctg ttcagcatcg   10200
acaccacgac gggcatatcc gcgccgccga tcgggatgat cagggtgacg ccgatcagca   10260
gcgacagggc gaagatgccc cagaaggccc agatggccga accgccgctg gcgaccagca   10320
ccacgatcag ggccacaatg gcgaccgcga tgatgatgtt cagcaggtga cgcgccggca   10380
gcaggatcgg agccccgccc atgttgccgt tcagcttggc gaaggcgatg accgaaccgg   10440
tgaaggtgat ggcgccgatg ccagacccca gcgacagctc gatcaggctg gcgccgtgga   10500
tggcgccgtc ttcgcccacg atgccatagg cggcgggcgt gtagatggcg ccacggcca    10560
ccagacaggc ggccatgccg accaggctgt ggaaggcggc gaccagttgc ggcatcgagg   10620
tcatggcgac ccggcgggcg atcaccgccc gaccgcgcc cccgacggcg acgccgccaa    10680
ggatcagacc aagggtcacg gcgtccagag cgccctggct ccagagcgtg ccagggtgg    10740
tgccgacagc gatggccatg ccgatcatgc cgttacggtt gccgtctgg ctggtcaccg    10800
ggctggacag gccgcgaagg gcgaggatga aaagcacccc ggagacgagg tacaggatag   10860
cggcgagatt ggcgttcatt ggactggttc cccctgctct cgcccgctca cttcttctct   10920
ttcttcttgt acatcgccag catgcgctgg gtgaccaaga agccgccgaa gatgttgacc   10980
gccgcaaagg ccgcagcgat cgccgccgca cccttggaga tccaggtgga gccggagaca   11040
gcgccgccgg ccaggtctga gttggcgccg tgggcggcgg cggccagaag ggcgccgacg   11100
atgatcacga acgaaatggc gttggtcacg gccatcagcg gcgtgtgcag cgcgggcgtc   11160
acgctccaga cgacgtagta gccgacgaag atggcgagca cgaagatcgc cagacggaac   11220
acggtggggt cgacggcttc cataggagcc tcccttttcga ttctggagtt aggcggtctt   11280
caggttcgga tgcacgatcg cgccgtcacg gatgacgaca gcggcctgca ggatctcgtc   11340
ctcgaaattg ggggcgaaag cgccctcctt gttcgtgaac agcgacgaca gggcgaagag   11400
gttgcgggcg tagagcgcgc tggcgtcggc ggcgatgcgc cccggcaggt tggcatgacc   11460
```

-continued

```
caggatcttg acgccgcctt cggtcacgac cgtctcgttg agcttggcgc cctcgacatt    11520
gccgccctgc tcgatcgcca gatcgaccag gatcgagccc ggcttcatcg acgcgacctg    11580
ggcggcgctg accagcttcg gcgcggggcg gcccgggatc agggccgtgg tgatgacgat    11640
gtcctgcttg gcgatgtggc tggagaccag ctcggcctgc ttggcctggt attccttgga    11700
catttccttg gcgtagccgc cggcggtctg ggcgttcttg aactcttcgt cctcgacggc    11760
caggaacttg gcgcccagcg actcgacctg ctccttggtg gccggacgca cgtcggtggc    11820
ggtcacgacc gcaccgaggc ggcgggccgt ggcgatggcc tgaaggcccg cgacgcccac    11880
gcccatgatg aacaccttgg ccgcggcgac ggtgccggcg gcggtcatca tcatcggcag    11940
ggccttgcca taggcttcgg cgccttcgat cacggcgcga tagccggcca ggttggcctg    12000
gctggacagc atgtccatca cctgcgcgcg ggtgatgcgc gggatgaact ccatggcgat    12060
cgccgtcgcc ccgccttgg ccagcgcgtc cagcgtttcc ttgtcctgat acggattgag    12120
cgctgcggcg acgatcgcgc cctttttgag cgccgcgatc tcggccgact caggcgcgcg    12180
caccttgaag aggacgtcgg cgtccttgag cgcgtccttg gcggtcttgg cgatcttggc    12240
gcccgccgcc tcgtagtcgg cgtccggata ggacgcggcc gtcccagctc cagcctggat    12300
cacaaccgag aacccggcgg cgccgagttt cttgaccgtt tcaggcgtag ccgcgacccg    12360
cgtttcgtcg gcgcgggtct ctttcgtgac ggcgatgacg gccatcggca ttcccctccc    12420
cagagcggtg ttacctcacc agcatgaggg gctctgtagg ggatagtctt gcctcttgtc    12480
gaggcatgac gtgcacg                                                  12497
```

```
<210> SEQ ID NO 28
<211> LENGTH: 28
<212> TYPE: DNA
<213> ORGANISM: Caulobacter crescentus

<400> SEQUENCE: 28
tcaaacatta cagactgttt agaatatt                                             28

<210> SEQ ID NO 29
<211> LENGTH: 28
<212> TYPE: DNA
<213> ORGANISM: Caulobacter crescentus

<400> SEQUENCE: 29
cgcgtcatga ctgaggtgta acgagact                                             28

<210> SEQ ID NO 30
<211> LENGTH: 200
<212> TYPE: DNA
<213> ORGANISM: Caulobacter crescentus

<400> SEQUENCE: 30
cctttgcaaa ccatatactc aaacgaccca agcaatatgg tcacaaaaac ttcaaacatt      60
acagactgtt tagaatatta agccccgta attctcttaa ttacgcgtca tgactgaggt      120
gtaacgagac ttcgcgagaa cccgaatgta tccaatattc atcggcgcag cgaacagcgc     180
ccagccagag ggatacttca                                                 200
```